(12) United States Patent
Nakatani et al.

(10) Patent No.: US 7,256,298 B2
(45) Date of Patent: Aug. 14, 2007

(54) PYRAZOLE DERIVATIVES AND PROCESS FOR THE PRODUCTION THEREOF

(75) Inventors: Masao Nakatani, Shizuoka (JP); Minoru Ito, Shizuoka (JP); Masahiro Miyazaki, Shizuoka (JP)

(73) Assignees: Ihara Chemical Industry Co., Ltd. (JP); Kumiai Chemical Industry Co., Ltd. (JP)

( * ) Notice: Subject to any disclaimer, the term of this patent is extended or adjusted under 35 U.S.C. 154(b) by 453 days.

(21) Appl. No.: 10/521,593

(22) PCT Filed: Jul. 31, 2003

(86) PCT No.: PCT/JP03/09762

§ 371 (c)(1),
(2), (4) Date: Jan. 18, 2005

(87) PCT Pub. No.: WO2004/013106

PCT Pub. Date: Feb. 12, 2004

(65) Prior Publication Data

US 2005/0215797 A1    Sep. 29, 2005

(30) Foreign Application Priority Data

Aug. 1, 2002 (JP) .............................. 2002-225083

(51) Int. Cl.
*C07D 231/18* (2006.01)
(52) U.S. Cl. ................................. 548/366.1; 548/366.4
(58) Field of Classification Search ............. 548/366.1, 548/366.4
See application file for complete search history.

(56) References Cited

U.S. PATENT DOCUMENTS 5,536,701 A   7/1996   Moedritzer et al. ......... 504/238
5,763,359 A   6/1998   Costales et al. ............ 504/251

FOREIGN PATENT DOCUMENTS

JP    2002-308857    10/2002

OTHER PUBLICATIONS

Gaede, B.J., J. Heterocyclic Chem. 30(1), pp. 49-54 (1993).
Hamper, B.C., J. Org. Chem. 57(21) pp. 5680-5686 (1992).
Park, K.H., Bull. Korean Chem. Soc., 17(2) pp. 113-114 (1996).
Hwang, K.J., Heterocycles 36(6), pp. 13775-13780, (1993).
Hwang, K.J., Korean J. of Med. Chem 2(2), pp. 122-126, (1992).
Kees, K.L., J. Med. Chem. 39(20) pp. 3920-3928 (1996).
Hein, F., J.C.S. Chem. Comm. (18) pp. 792-793 (1979).

*Primary Examiner*—Kamal A. Saeed
(74) *Attorney, Agent, or Firm*—Bacon & Thomas, PLLC

(57) ABSTRACT

The present invention provides pyrazole derivatives useful as production intermediates for isoxazoline derivatives having an excellent herbicidal effect and selectivity between crops and weeds as well as processes for producing the same.

The pyrazole derivatives or pharmaceutically acceptable salts thereof which are inventive compounds are represented by the general formula [I] or a salt thereof:

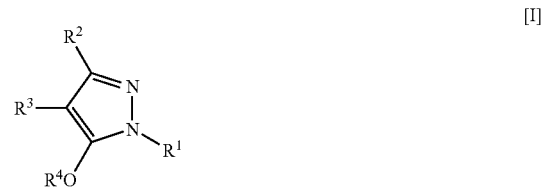

wherein $R^1$ represents a C1 to C6 alkyl group, $R^2$ represents a C1 to C3 haloalkyl group, $R^3$ represents a hydrogen atom, a C1 to C3 alkyl group which may be substituted with one or more substituents selected from the following substituent group α, or a formyl group, $R^4$ represents a hydrogen atom or a C1 to C3 haloalkyl group, provided that $R^4$ represents a C1 to C3 haloalkyl group in the case that $R^3$ is a hydrogen or a formyl group, and $R^4$ is a hydrogen group or a C1 to C3 haloalkyl group in the case that $R^3$ is a C1 to C3 alkyl group which may be substituted with one or more substituents selected from the following substituent group α.

6 Claims, No Drawings

PYRAZOLE DERIVATIVES AND PROCESS FOR THE PRODUCTION THEREOF

CROSS-REFERENCE TO RELATED APPLICATIONS

This application is a National Phase Application (35 USC 371) of PCT/JP2003/009762 filed Jul. 31, 2003 and claims priority of Japanese Application No. 2002-225083 filed Aug. 1, 2002.

TECHNICAL FIELD

The present invention relates to pyrazole derivatives useful as production intermediates for agrochemicals and medicaments.

BACKGROUND ART

As a process for producing an isoxazoline derivative useful as a herbicide, for example, Japanese Patent Laid-Open No. 308857/2002 discloses Production Examples of isoxazoline derivatives having a pyrazole ring wherein starting material having an isoxazoline ring is reacted with sodium hydrosulfide hydrate, followed by a reaction with 4-bromomethyl-5-chloro-1-phenyl-3-trifluoromethyl-1H-pyrazole in the presence of potassium carbonate and Rongalit.

An object of the invention is to provide useful production intermediates for the above isoxazoline derivatives and processes for production of the intermediates.

DISCLOSURE OF THE INVENTION

As a result of the extensive studies for solving the above problems, the present inventors have found that the above isoxazoline derivatives can be produced more efficiently and conveniently by using specific pyrazole derivatives capable of being produced from easily available starting materials as production intermediates. Thus, they have realized that the pyrazole derivatives become production intermediates extremely useful in the production of the above isoxazoline derivatives and hence have accomplished the invention.

Namely, the present invention solves the above problems by providing the inventions of the following (1) to (15).

(1) A pyrazole derivative represented by the general formula [I] or a salt thereof:

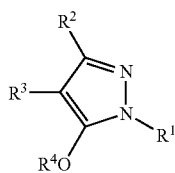

[I]

wherein $R^1$ represents a C1 to C6 alkyl group, $R^2$ represents a C1 to C3 haloalkyl group, $R^3$ represents a hydrogen atom, a C1 to C3 alkyl group which may be substituted with one or more substituents selected from the following substituent group α, or a formyl group, $R^4$ represents a hydrogen atom or a C1 to C3 haloalkyl group, provided that $R^4$ represents a C1 to C3 haloalkyl group in the case that $R^3$ is a hydrogen atom or a formyl group and $R^4$ is a hydrogen atom or a C1 to C3 haloalkyl group in the case that $R^3$ is a C1 to C3 alkyl group which may be substituted with one or more substituents selected from the following substituent group α; "Substituent group α"

halogen atoms, —SH group, —SC(═NH)NH$_2$ group (2) The pyrazole derivative or salt thereof according to (1), wherein $R^4$ is a C1 to C3 haloalkyl group.

(3) The pyrazole derivative or salt thereof according to (1), wherein $R^3$ is a C1 to C3 alkyl group and $R^4$ is a hydrogen atom.

(4) The pyrazole derivative or salt thereof according to (1), wherein $R^3$ is a methyl group which may be substituted with one or more substituents selected from the substituent group α.

(5) The pyrazole derivative or salt thereof according to (3), wherein $R^3$ is a methyl group.

(6) A process for producing a pyrazole derivative represented by the general formula [3], comprising a step of reacting a compound represented by the general formula [1] with a compound represented by the general formula [2]:

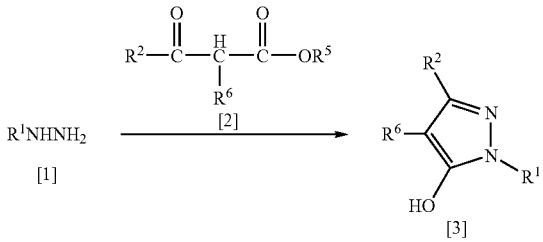

wherein $R^1$ and $R^2$ represent the same meanings as mentioned above, $R^5$ represents a C1 to C3 alkyl group, a phenyl group which may be substituted, or a benzyl group which may be substituted, and $R^6$ is a C1 to C3 alkyl group.

(7) A process for producing a pyrazole derivative represented by the general formula [6], comprising a step of reacting a compound represented by the general formula [4] with a compound represented by the general formula [5] in the presence of a base:

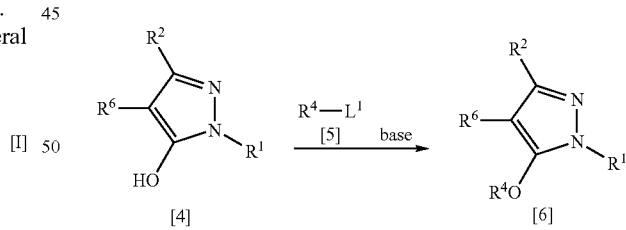

wherein $R^1$, $R^2$, $R^4$, and $R^6$ represent the same meanings as mentioned above, and $L^1$ is a leaving group which is more reactive than a halogen atom remaining after haloalkylation and represents a halogen atom, a C1 to C3 alkylsulfonyloxy group, a C1 to C3 haloalkylsulfonyloxy group, a phenylsulfonyloxy group which may be substituted, or a benzylsulfonyloxy group which may be substituted, and the like.

(8) A process for producing a pyrazole derivative represented by the general formula [6], comprising a step of reacting a compound represented by the general formula [4] with triphenylphosphine, a compound represented by the general formula [7], and an azo compound [8]:

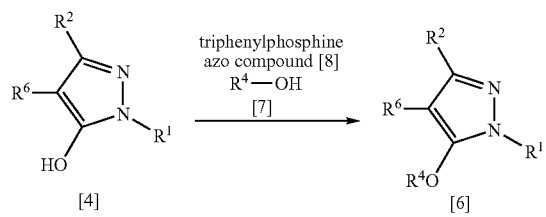

wherein $R^1$, $R^2$, $R^4$, and $R^6$ represent the same meanings as mentioned above.

(9) A process for producing a pyrazole derivative represented by the general formula [10], comprising a step of reacting a compound represented by the general formula [9] with a halogenating agent:

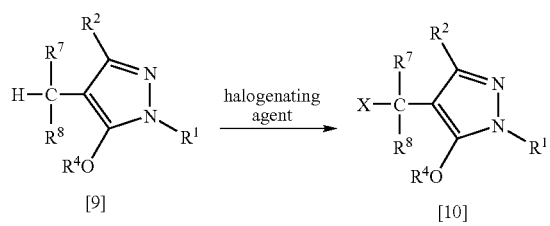

wherein $R^1$, $R^2$, and $R^4$ represent the same meanings as mentioned above, $R^7$ and $R^8$ each represents a hydrogen atom or a C1 to C2 alkyl group, and X is a halogen atom.

(10) A process for producing a pyrazole derivative represented by the general formula [12], comprising a step of reacting a compound represented by the general formula [10] with a compound represented by the general formula [11]:

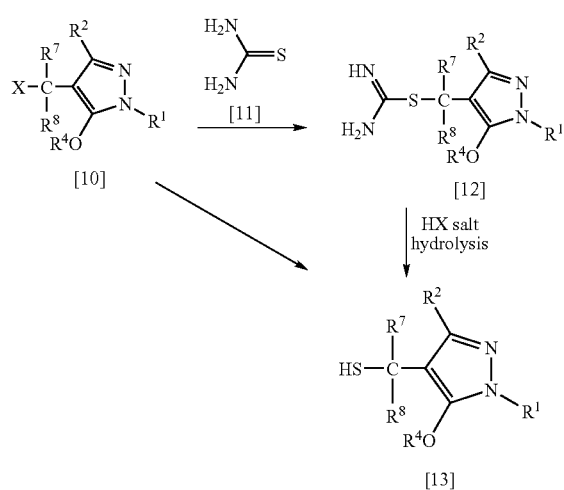

wherein $R^1$, $R^2$, $R^4$, $R^7$, $R^8$, and X represent the same meanings as mentioned above.

(11) The process for producing a pyrazole derivative represented by the general formula [13], wherein the compound represented by the general formula [12] according to the above (10) is hydrolyzed.

(12) The process for producing a pyrazole derivative represented by the general formula [13], wherein the compound represented by the general formula [10] according to the above (10) is reacted with a sulfide.

(13) A process for producing a pyrazole derivative represented by the general formula [15], comprising a step of formylating a compound represented by the general formula [14]:

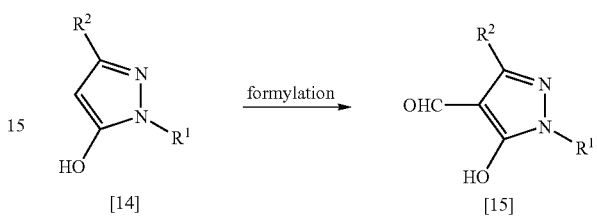

wherein $R^1$ and $R^2$ represent the same meanings as mentioned above.

(14) A process for producing a pyrazole derivative represented by the general formula [17], comprising a step of reacting a compound represented by the general formula [16] with a compound represented by the general formula [5] in the presence of a base:

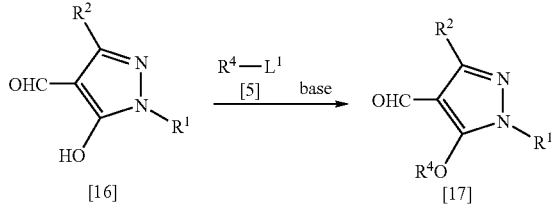

wherein $R^1$, $R^2$, $R^4$, and $L^1$ represent the same meanings as mentioned above.

(15) A process for producing a pyrazole derivative represented by the general formula [19], comprising a step of halomethylating a compound represented by the general formula [18]:

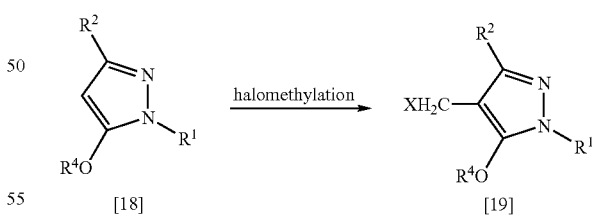

wherein $R^1$, $R^2$, $R^4$, and X represent the same meanings as mentioned above.

Incidentally, the definitions of the terms used in the present specification are given below.

The expression of "C1 to C6" and the like indicates that a substituent appearing after the expression has 1 to 6 carbon atoms in the case of "C1 to C6".

The halogen atom refers to a fluorine atom, a chlorine atom, a bromine atom, or an iodine atom.

The C1 to C3 alkyl group refers, unless otherwise specified, to a linear or branched alkyl group having 1 to 3 carbon atoms, and examples thereof include a methyl group, an ethyl group, an n-propyl group, an iso-propyl group, and the like.

The C1 to C6 alkyl group refers, unless otherwise specified, to a linear or branched alkyl group having 1 to 6 carbon atoms, and examples thereof include a methyl group, an ethyl group, an n-propyl group, an iso-propyl group, an n-butyl group, an isobutyl group, a sec-butyl group, a tert-butyl group, an n-pentyl group, an iso-pentyl group, a neopentyl group, an n-hexyl group, an iso-hexyl group, a 3,3-dimethylbutyl group, and the like.

The C1 to C3 haloalkyl group refers, unless otherwise specified, to a linear or branched alkyl group having 1 to 3 carbon atoms, which is substituted with 1 to 7 halogen atoms which are the same or different from one another, and examples thereof include a fluoromethyl group, a chloromethyl group, a bromomethyl group, a difluoromethyl group, a trifluoromethyl group, a dichlorofluoromethyl group, a chlorodifluoromethyl group, a 2,2-difluoroethyl group, a 2,2,2-trifluoroethyl group, a pentafluoroethyl group, a 1-fluoro-1-methylethyl group, a 1-trifluoromethyl-2,2,2-trifluoroethyl group, and the like.

The C1 to C4 alkylsulfonyloxy group refers to a (C1 to C4 alkyl)—$SO_2$—O— group wherein the alkyl moiety represents the same meaning as mentioned above, and examples thereof include a methanesulfonyloxy group, an ethanesulfonyloxy group, and the like.

The C1 to C3 haloalkylsulfonyloxy group refers to a (C1 to C3 haloalkyl)—$SO_2$—O— group wherein the haloalkyl moiety represents the same meaning as mentioned above, and examples thereof include a trifluoromethanesulfonyloxy group, a trichloromethanesulfonyloxy group, and the like.

The "group which may be substituted" in the phenyl group (which may be substituted), the phenylsulfonyloxy group (which may be substituted), the benzyl group (which may be substituted), or the benzylsulfonyloxy group (which may be substituted) refers to a group which may be substituted with, for example, a halogen atom, a C1 to C10 alkyl group, a C1 to C4 haloalkyl group, a C1 to C10 alkoxyalkyl group, a C1 to C10 alkoxy group, a C1 to C10 alkylthio group, a C1 to C10 alkylsulfonyl group, an acyl group, a C1 to C10 alkoxycarbonyl group, a cyano group, a carbamoyl group (a nitrogen atom thereof may be substituted with 1 to C10 alkyl groups which are the same or different from each other), a nitro group, or an amino group (a nitrogen atom thereof may be substituted with C1 to C10 alkyl groups, C1 to C6 acyl groups, C1 to C4 haloalkylcarbonyl groups, C1 to C10 alkylsulfonyl groups, and C1 to C4 haloalkylsulfonyl groups, which are the same or different from each other).

The salt is a salt of a compound of the general formula [I] wherein a hydroxyl group, an —SH group, an —SC(=NH)$NH_2$ group, or the like is present in the structure, with a metal or an organic base or with a mineral acid or an organic acid. The metal in this case includes alkali metals such as sodium and potassium and alkaline earth metals such as magnesium and calcium. The organic base includes triethylamine and diisopropylamine. The mineral acid includes hydrochloric acid, hydrobromic acid, sulfuric acid, and the like. The organic acid includes acetic acid, methanesulfonic acid, p-toluenesulfonic acid, and the like.

BEST MODE FOR CARRYING OUT THE INVENTION

Next, representative examples of the pyrazole derivatives represented by the general formula [I] or salt thereof (the inventive compounds) are shown in Tables 1 to 11. However, the compounds of the present invention are not restricted to these examples.

The following representations in the tables in the present specification represent the respective corresponding groups as shown below.

Me: methyl group
Et: ethyl group
Pr-n: n-propyl group
Pr-i: iso-propyl group
Bu-n: n-butyl group
Bu-i: iso-butyl group
Bu-s: sec-butyl group
Bu-t: tert-butyl group
Pen-n: n-pentyl group
Hex-n: n-hexyl group When the compound of the present invention contains a hydroxyl group as a substituent, there may exist compounds having keto-enol tautomers. Any of the tautomers and any mixtures thereof are included in the compounds of the present invention.

TABLE 1

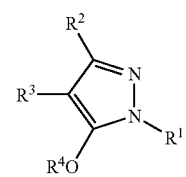

[I]

| Compound No. | $R^1$ | $R^2$ | $R^3$ | $R^4$ |
|---|---|---|---|---|
| 001 | Me | $CF_3$ | H | $CHF_2$ |
| 002 | Me | $CF_3$ | H | $CH_2CHF_2$ |
| 003 | Me | $CF_3$ | H | $CH_2CF_3$ |
| 004 | Me | $CHF_2$ | H | $CHF_2$ |
| 005 | Me | $CHF_2$ | H | $CH_2CHF_2$ |
| 006 | Me | $CHF_2$ | H | $CH_2CF_3$ |
| 007 | Me | $CClF_2$ | H | $CHF_2$ |
| 008 | Me | $CClF_2$ | H | $CH_2CHF_2$ |
| 009 | Et | $CF_3$ | H | $CHF_2$ |
| 010 | Et | $CF_3$ | H | $CH_2CHF_2$ |
| 011 | Et | $CF_3$ | H | $CH_2CF_3$ |

TABLE 2

| Compound No. | $R^1$ | $R^2$ | $R^3$ | $R^4$ |
|---|---|---|---|---|
| 012 | Et | $CHF_2$ | H | $CHF_2$ |
| 013 | Et | $CHF_2$ | H | $CH_2CHF_2$ |
| 014 | Et | $CHF_2$ | H | $CH_2CF_3$ |
| 015 | Pr-i | $CF_3$ | H | $CHF_2$ |
| 016 | Pr-i | $CF_3$ | H | $CH_2CHF_2$ |
| 017 | Pr-i | $CF_3$ | H | $CH_2CF_3$ |
| 018 | Pr-n | $CF_3$ | H | $CHF_2$ |
| 019 | Pr-n | $CF_3$ | H | $CH_2CHF_2$ |
| 020 | Pr-n | $CF_3$ | H | $CH_2CF_3$ |
| 021 | Bu-t | $CF_3$ | H | $CHF_2$ |
| 022 | Bu-t | $CF_3$ | H | $CH_2CHF_2$ |
| 023 | Bu-t | $CF_3$ | H | $CH_2CF_3$ |
| 024 | Pen-n | $CF_3$ | H | $CHF_2$ |
| 025 | Hex-n | $CF_3$ | H | $CHF_2$ |
| 026 | Me | $CF_3$ | CHO | $CHF_2$ |
| 027 | Me | $CHF_2$ | CHO | $CHF_2$ |

TABLE 2-continued

| Compound No. | $R^1$ | $R^2$ | $R^3$ | $R^4$ |
| --- | --- | --- | --- | --- |
| 028 | Me | $CF_3$ | CHO | $CH_2CHF_2$ |
| 029 | Me | $CF_3$ | CHO | $CH_2CF_3$ |
| 030 | Et | $CF_3$ | CHO | $CHF_2$ |
| 031 | Et | $CF_3$ | CHO | $CH_2CHF_2$ |
| 032 | Pr-i | $CF_3$ | CHO | $CHF_2$ |
| 033 | Pr-i | $CF_3$ | CHO | $CH_2CHF_2$ |
| 034 | Bu-t | $CF_3$ | CHO | $CHF_2$ |
| 035 | Bu-t | $CF_3$ | CHO | $CH_2CHF_2$ |

TABLE 3

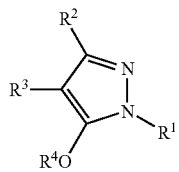

| Compound No. | $R^1$ | $R^2$ | $R^3$ | $R^4$ |
| --- | --- | --- | --- | --- |
| 036 | Me | $CF_3$ | Me | H |
| 037 | Et | $CF_3$ | Me | H |
| 038 | Pr-i | $CF_3$ | Me | H |
| 039 | Pr-n | $CF_3$ | Me | H |
| 040 | Bu-n | $CF_3$ | Me | H |
| 041 | Bu-s | $CF_3$ | Me | H |
| 042 | Bu-i | $CF_3$ | Me | H |
| 043 | Bu-t | $CF_3$ | Me | H |
| 044 | Pen-n | $CF_3$ | Me | H |
| 045 | Hex-n | $CF_3$ | Me | H |
| 046 | Me | $CHF_2$ | Me | H |
| 047 | Et | $CHF_2$ | Me | H |
| 048 | Pr-i | $CHF_2$ | Me | H |
| 049 | Pr-n | $CHF_2$ | Me | H |
| 050 | Bu-n | $CHF_2$ | Me | H |
| 051 | Bu-s | $CHF_2$ | Me | H |
| 052 | Bu-i | $CHF_2$ | Me | H |
| 053 | Bu-t | $CHF_2$ | Me | H |
| 054 | Pen-n | $CHF_2$ | Me | H |
| 055 | Hex-n | $CHF_2$ | Me | H |
| 056 | Me | $CF_3$ | Et | H |
| 057 | Et | $CF_3$ | Et | H |
| 058 | Pr-i | $CF_3$ | Et | H |
| 059 | Pen-n | $CF_3$ | Et | H |
| 060 | Hex-n | $CF_3$ | Et | H |
| 061 | Me | $CHF_2$ | Et | H |
| 062 | Et | $CHF_2$ | Et | H |
| 063 | Pr-i | $CHF_2$ | Et | H |
| 064 | Me | $CF_3$ | Pr-n | H |
| 065 | Et | $CF_3$ | Pr-n | H |
| 066 | Pr-i | $CF_3$ | Pr-n | H |

TABLE 4

| Compound No. | $R^1$ | $R^2$ | $R^3$ | $R^4$ |
| --- | --- | --- | --- | --- |
| 067 | Me | $CHF_2$ | Pr-n | H |
| 068 | Et | $CHF_2$ | Pr-n | H |
| 069 | Pr-i | $CHF_2$ | Pr-n | H |
| 070 | Me | $CF_3$ | Pr-i | H |
| 071 | Et | $CF_3$ | Pr-i | H |
| 072 | Pr-i | $CF_3$ | Pr-i | H |
| 073 | Me | $CHF_2$ | Pr-i | H |
| 074 | Et | $CHF_2$ | Pr-i | H |
| 075 | Pr-i | $CHF_2$ | Pr-i | H |
| 076 | Me | $CF_3$ | Me | $CHF_2$ |
| 077 | Me | $CHF_2$ | Me | $CHF_2$ |
| 078 | Me | $CF_3$ | Me | $CH_2CHF_2$ |
| 079 | Me | $CF_3$ | Me | $CH_2CF_3$ |
| 080 | Et | $CF_3$ | Me | $CHF_2$ |

TABLE 4-continued

| Compound No. | $R^1$ | $R^2$ | $R^3$ | $R^4$ |
| --- | --- | --- | --- | --- |
| 081 | Et | $CHF_2$ | Me | $CHF_2$ |
| 082 | Et | $CF_3$ | Me | $CH_2CHF_2$ |
| 083 | Et | $CF_3$ | Me | $CH_2CF_3$ |
| 084 | Pr-i | $CF_3$ | Me | $CHF_2$ |
| 085 | Pr-i | $CHF_2$ | Me | $CHF_2$ |
| 086 | Pr-i | $CF_3$ | Me | $CH_2CHF_2$ |
| 087 | Pr-i | $CF_3$ | Me | $CH_2CF_3$ |
| 088 | Pr-n | $CF_3$ | Me | $CHF_2$ |
| 089 | Pr-n | $CF_3$ | Me | $CH_2CHF_2$ |
| 090 | Pr-n | $CF_3$ | Me | $CH_2CF_3$ |
| 091 | Bu-n | $CF_3$ | Me | $CHF_2$ |
| 092 | Bu-n | $CF_3$ | Me | $CH_2CHF_2$ |
| 093 | Bu-n | $CF_3$ | Me | $CH_2CF_3$ |
| 094 | Bu-i | $CF_3$ | Me | $CHF_2$ |
| 095 | Bu-i | $CF_3$ | Me | $CH_2CHF_2$ |
| 096 | Bu-i | $CF_3$ | Me | $CH_2CF_3$ |
| 097 | Bu-s | $CF_3$ | Me | $CHF_2$ |
| 098 | Bu-s | $CF_3$ | Me | $CH_2CHF_2$ |
| 099 | Bu-s | $CF_3$ | Me | $CH_2CF_3$ |
| 100 | Bu-t | $CF_3$ | Me | $CHF_2$ |
| 101 | Bu-t | $CF_3$ | Me | $CH_2CHF_2$ |

TABLE 5

| Compound No. | $R^1$ | $R^2$ | $R^3$ | $R^4$ |
| --- | --- | --- | --- | --- |
| 102 | Bu-t | $CF_3$ | Me | $CH_2CF_3$ |
| 103 | Pen-n | $CF_3$ | Me | $CHF_2$ |
| 104 | Hex-n | $CF_3$ | Me | $CHF_2$ |
| 105 | Me | $CF_3$ | Et | $CHF_2$ |
| 106 | Me | $CF_3$ | Et | $CH_2CHF_2$ |
| 107 | Et | $CF_3$ | Et | $CHF_2$ |
| 108 | Et | $CF_3$ | Et | $CH_2CHF_2$ |
| 109 | Pr-i | $CF_3$ | Et | $CHF_2$ |
| 110 | Pr-i | $CF_3$ | Et | $CH_2CHF_2$ |
| 111 | Me | $CF_3$ | Pr-n | $CHF_2$ |
| 112 | Me | $CF_3$ | Pr-n | $CH_2CHF_2$ |
| 113 | Et | $CF_3$ | Pr-n | $CHF_2$ |
| 114 | Et | $CF_3$ | Pr-n | $CH_2CHF_2$ |
| 115 | Pr-i | $CF_3$ | Pr-n | $CHF_2$ |
| 116 | Pr-i | $CF_3$ | Pr-n | $CH_2CHF_2$ |
| 117 | Me | $CF_3$ | Pr-i | $CHF_2$ |
| 118 | Me | $CF_3$ | Pr-i | $CH_2CHF_2$ |
| 119 | Et | $CF_3$ | Pr-i | $CHF_2$ |
| 120 | Et | $CF_3$ | Pr-i | $CH_2CHF_2$ |
| 121 | Pr-i | $CF_3$ | Pr-i | $CHF_2$ |
| 122 | Pr-i | $CF_3$ | Pr-i | $CH_2CHF_2$ |
| 123 | Me | $CF_3$ | $CH_2Cl$ | $CHF_2$ |
| 124 | Me | $CHF_2$ | $CH_2Cl$ | $CHF_2$ |
| 125 | Me | $CF_3$ | $CH_2Cl$ | $CH_2CHF_2$ |
| 126 | Me | $CF_3$ | $CH_2Cl$ | $CH_2CF_3$ |
| 127 | Et | $CF_3$ | $CH_2Cl$ | $CHF_2$ |
| 128 | Et | $CF_3$ | $CH_2Cl$ | $CH_2CHF_2$ |
| 129 | Et | $CF_3$ | $CH_2Cl$ | $CH_2CF_3$ |
| 130 | Pr-i | $CF_3$ | $CH_2Cl$ | $CHF_2$ |
| 131 | Pr-i | $CF_3$ | $CH_2Cl$ | $CH_2CHF_2$ |
| 132 | Pr-i | $CF_3$ | $CH_2Cl$ | $CH_2CF_3$ |
| 133 | Pr-n | $CF_3$ | $CH_2Cl$ | $CHF_2$ |
| 134 | Pr-n | $CF_3$ | $CH_2Cl$ | $CH_2CHF_2$ |
| 135 | Pr-n | $CF_3$ | $CH_2Cl$ | $CH_2CF_3$ |
| 136 | Bu-n | $CF_3$ | $CH_2Cl$ | $CHF_2$ |

TABLE 6

| Compound No. | $R^1$ | $R^2$ | $R^3$ | $R^4$ |
| --- | --- | --- | --- | --- |
| 137 | Bu-n | $CF_3$ | $CH_2Cl$ | $CH_2CHF_2$ |
| 138 | Bu-n | $CF_3$ | $CH_2Cl$ | $CH_2CF_3$ |
| 140 | Bu-t | $CF_3$ | $CH_2Cl$ | $CHF_2$ |
| 141 | Bu-t | $CF_3$ | $CH_2Cl$ | $CH_2CHF_2$ |
| 142 | Bu-t | $CF_3$ | $CH_2Cl$ | $CH_2CF_3$ |
| 143 | Me | $CF_3$ | CH(Me)Cl | $CHF_2$ |

TABLE 6-continued

| Compound No. | R¹ | R² | R³ | R⁴ |
|---|---|---|---|---|
| 144 | Me | CHF₂ | CH(Me)Cl | CHF₂ |
| 145 | Me | CF₃ | CH(Me)Cl | CH₂CHF₂ |
| 146 | Me | CF₃ | CH(Me)Cl | CH₂CF₃ |
| 147 | Me | CF₃ | CH(Et)Cl | CHF₂ |
| 148 | Me | CHF₂ | CH(Et)Cl | CHF₂ |
| 149 | Me | CF₃ | CH(Et)Cl | CH₂CHF₂ |
| 150 | Me | CF₃ | CH(Et)Cl | CH₂CF₃ |
| 151 | Me | CF₃ | CH₂Br | CHF₂ |
| 152 | Me | CHF₂ | CH₂Br | CHF₂ |
| 153 | Me | CF₃ | CH₂Br | CH₂CHF₂ |
| 154 | Me | CF₃ | CH₂Br | CH₂CF₃ |
| 155 | Et | CF₃ | CH₂Br | CHF₂ |
| 156 | Et | CF₃ | CH₂Br | CH₂CHF₂ |
| 157 | Et | CF₃ | CH₂Br | CH₂CF₃ |
| 158 | Pr-i | CF₃ | CH₂Br | CHF₂ |
| 159 | Pr-i | CF₃ | CH₂Br | CH₂CHF₂ |
| 160 | Pr-i | CF₃ | CH₂Br | CH₂CF₃ |
| 161 | Pr-n | CF₃ | CH₂Br | CHF₂ |
| 162 | Pr-n | CF₃ | CH₂Br | CH₂CHF₂ |
| 163 | Pr-n | CF₃ | CH₂Br | CH₂CF₃ |
| 164 | Bu-n | CF₃ | CH₂Br | CHF₂ |
| 165 | Bu-n | CF₃ | CH₂Br | CH₂CHF₂ |
| 166 | Bu-n | CF₃ | CH₂Br | CH₂CF₃ |
| 167 | Bu-t | CF₃ | CH₂Br | CHF₂ |
| 168 | Bu-t | CF₃ | CH₂Br | CH₂CHF₂ |
| 169 | Bu-t | CF₃ | CH₂Br | CH₂CF₃ |
| 170 | Me | CF₃ | CH(Me)Br | CHF₂ |
| 171 | Me | CHF₂ | CH(Me)Br | CHF₂ |
| 172 | Me | CF₃ | CH(Me)Br | CH₂CHF₂ |

TABLE 7

| Compound No. | R¹ | R² | R³ | R⁴ |
|---|---|---|---|---|
| 173 | Me | CF₃ | CH(Me)Br | CH₂CF₃ |
| 174 | Me | CF₃ | CH(Et)Br | CHF₂ |
| 175 | Me | CHF₂ | CH(Et)Br | CHF₂ |
| 176 | Me | CF₃ | CH(Et)Br | CH₂CHF₂ |
| 177 | Me | CF₃ | CH(Et)Br | CH₂CF₃ |
| 178 | Me | CF₃ | CH₂SC(=NH)NH₂HCl salt | CHF₂ |
| 179 | Me | CHF₂ | CH₂SC(=NH)NH₂HCl salt | CHF₂ |
| 180 | Me | CF₃ | CH₂SC(=NH)NH₂HCl salt | CH₂CHF₂ |
| 181 | Me | CF₃ | CH₂SC(=NH)NH₂HCl salt | CH₂CF₃ |
| 182 | Et | CF₃ | CH₂SC(=NH)NH₂HCl salt | CHF₂ |
| 183 | Et | CF₃ | CH₂SC(=NH)NH₂HCl salt | CH₂CHF₂ |
| 184 | Et | CF₃ | CH₂SC(=NH)NH₂HCl salt | CH₂CF₃ |
| 185 | Pr-i | CF₃ | CH₂SC(=NH)NH₂HCl salt | CHF₂ |
| 186 | Pr-i | CF₃ | CH₂SC(=NH)NH₂HCl salt | CH₂CHF₂ |
| 187 | Pr-i | CF₃ | CH₂SC(=NH)NH₂HCl salt | CH₂CF₃ |
| 188 | Pr-n | CF₃ | CH₂SC(=NH)NH₂HCl salt | CHF₂ |
| 189 | Pr-n | CF₃ | CH₂SC(=NH)NH₂HCl salt | CH₂CHF₂ |
| 190 | Pr-n | CF₃ | CH₂SC(=NH)NH₂HCl salt | CH₂CF₃ |
| 191 | Bu-n | CF₃ | CH₂SC(=NH)NH₂HCl salt | CHF₂ |
| 192 | Bu-n | CF₃ | CH₂SC(=NH)NH₂HCl salt | CH₂CHF₂ |
| 193 | Bu-n | CF₃ | CH₂SC(=NH)NH₂HCl salt | CH₂CF₃ |
| 194 | Bu-t | CF₃ | CH₂SC(=NH)NH₂HCl salt | CHF₂ |
| 195 | Bu-t | CF₃ | CH₂SC(=NH)NH₂HCl salt | CH₂CHF₂ |
| 196 | Bu-t | CF₃ | CH₂SC(=NH)NH₂HCl salt | CH₂CF₃ |
| 197 | Me | CF₃ | CH₂SC(=NH)NH₂HBr salt | CHF₂ |
| 198 | Me | CHF₂ | CH₂SC(=NH)NH₂HBr salt | CHF₂ |
| 199 | Me | CF₃ | CH₂SC(=NH)NH₂HBr salt | CH₂CHF₂ |
| 200 | Me | CF₃ | CH₂SC(=NH)NH₂HBr salt | CH₂CF₃ |
| 201 | Et | CF₃ | CH₂SC(=NH)NH₂HBr salt | CHF₂ |
| 202 | Et | CF₃ | CH₂SC(=NH)NH₂HBr salt | CH₂CHF₂ |
| 203 | Et | CF₃ | CH₂SC(=NH)NH₂HBr salt | CH₂CF₃ |
| 204 | Pr-i | CF₃ | CH₂SC(=NH)NH₂HBr salt | CHF₂ |
| 205 | Pr-i | CF₃ | CH₂SC(=NH)NH₂HBr salt | CH₂CHF₂ |
| 206 | Pr-i | CF₃ | CH₂SC(=NH)NH₂HBr salt | CH₂CF₃ |
| 207 | Pr-n | CF₃ | CH₂SC(=NH)NH₂HBr salt | CHF₂ |

TABLE 8

| Compound No. | R¹ | R² | R³ | R⁴ |
|---|---|---|---|---|
| 208 | Pr-n | CF₃ | CH₂SC(=NH)NH₂HBr salt | CH₂CHF₂ |
| 209 | Pr-n | CF₃ | CH₂SC(=NH)NH₂HBr salt | CH₂CF₃ |
| 210 | Bu-n | CF₃ | CH₂SC(=NH)NH₂HBr salt | CHF₂ |
| 211 | Bu-n | CF₃ | CH₂SC(=NH)NH₂HBr salt | CH₂CHF₂ |
| 212 | Bu-n | CF₃ | CH₂SC(=NH)NH₂HBr salt | CH₂CF₃ |
| 213 | Bu-t | CF₃ | CH₂SC(=NH)NH₂HBr salt | CHF₂ |
| 214 | Bu-t | CF₃ | CH₂SC(=NH)NH₂HBr salt | CH₂CHF₂ |
| 215 | Bu-t | CF₃ | CH₂SC(=NH)NH₂HBr salt | CH₂CF₃ |
| 216 | Me | CF₃ | CH₂SH | CHF₂ |
| 217 | Me | CHF₂ | CH₂SH | CHF₂ |
| 218 | Me | CF₃ | CH₂SH | CH₂CHF₂ |
| 219 | Me | CF₃ | CH₂SH | CH₂CF₃ |
| 220 | Et | CF₃ | CH₂SH | CHF₂ |
| 221 | Et | CF₃ | CH₂SH | CH₂CHF₂ |
| 222 | Et | CF₃ | CH₂SH | CH₂CF₃ |
| 223 | Pr-i | CF₃ | CH₂SH | CHF₂ |
| 224 | Pr-i | CF₃ | CH₂SH | CH₂CHF₂ |
| 225 | Pr-i | CF₃ | CH₂SH | CH₂CF₃ |
| 226 | Pr-n | CF₃ | CH₂SH | CHF₂ |
| 227 | Pr-n | CF₃ | CH₂SH | CH₂CHF₂ |
| 228 | Pr-n | CF₃ | CH₂SH | CH₂CF₃ |
| 229 | Bu-n | CF₃ | CH₂SH | CHF₂ |
| 230 | Bu-n | CF₃ | CH₂SH | CH₂CHF₂ |
| 231 | Bu-n | CF₃ | CH₂SH | CH₂CF₃ |
| 232 | Bu-t | CF₃ | CH₂SH | CHF₂ |
| 233 | Bu-t | CF₃ | CH₂SH | CH₂CHF₂ |
| 234 | Bu-t | CF₃ | CH₂SH | CH₂CF₃ |
| 235 | Me | CF₃ | CH(Me)SH | CHF₂ |
| 236 | Me | CHF₂ | CH(Me)SH | CHF₂ |
| 237 | Me | CF₃ | CH(Me)SH | CH₂CHF₂ |
| 238 | Me | CF₃ | CH(Me)SH | CH₂CF₃ |
| 239 | Me | CF₃ | CH(Et)SH | CHF₂ |
| 240 | Me | CHF₂ | CH(Et)SH | CHF₂ |
| 241 | Me | CF₃ | CH(Et)SH | CH₂CHF₂ |
| 242 | Me | CF₃ | CH(Et)SH | CH₂CF₃ |

TABLE 9

| Compound No. | R¹ | R² | R³ | R⁴ |
|---|---|---|---|---|
| 243 | Me | CF₃ | CH₂S⁻Na⁺ salt | CHF₂ |
| 244 | Me | CHF₂ | CH₂S⁻Na⁺ salt | CHF₂ |
| 245 | Me | CF₃ | CH₂S⁻Na⁺ salt | CH₂CHF₂ |
| 246 | Me | CF₃ | CH₂S⁻Na⁺ salt | CH₂CF₃ |
| 247 | Et | CF₃ | CH₂S⁻Na⁺ salt | CHF₂ |
| 248 | Et | CF₃ | CH₂S⁻Na⁺ salt | CH₂CHF₂ |
| 249 | Et | CF₃ | CH₂S⁻Na⁺ salt | CH₂CF₃ |
| 250 | Pr-i | CF₃ | CH₂S⁻Na⁺ salt | CHF₂ |
| 251 | Pr-i | CF₃ | CH₂S⁻Na⁺ salt | CH₂CHF₂ |
| 252 | Pr-i | CF₃ | CH₂S⁻Na⁺ salt | CH₂CF₃ |
| 253 | Pr-n | CF₃ | CH₂S⁻Na⁺ salt | CHF₂ |
| 254 | Pr-n | CF₃ | CH₂S⁻Na⁺ salt | CH₂CHF₂ |
| 255 | Pr-n | CF₃ | CH₂S⁻Na⁺ salt | CH₂CF₃ |
| 256 | Bu-n | CF₃ | CH₂S⁻Na⁺ salt | CHF₂ |
| 257 | Bu-n | CF₃ | CH₂S⁻Na⁺ salt | CH₂CHF₂ |
| 258 | Bu-n | CF₃ | CH₂S⁻Na⁺ salt | CH₂CF₃ |
| 259 | Bu-t | CF₃ | CH₂S⁻Na⁺ salt | CHF₂ |
| 260 | Bu-t | CF₃ | CH₂S⁻Na⁺ salt | CH₂CHF₂ |
| 261 | Bu-t | CF₃ | CH₂S⁻Na⁺ salt | CH₂CF₃ |
| 262 | Me | CF₃ | CH₂S⁻K⁺ salt | CHF₂ |
| 263 | Me | CHF₂ | CH₂S⁻K⁺ salt | CHF₂ |
| 264 | Me | CF₃ | CH₂S⁻K⁺ salt | CH₂CHF₂ |
| 265 | Me | CF₃ | CH₂S⁻K⁺ salt | CH₂CF₃ |
| 266 | Et | CF₃ | CH₂S⁻K⁺ salt | CHF₂ |
| 267 | Et | CF₃ | CH₂S⁻K⁺ salt | CH₂CHF₂ |
| 268 | Et | CF₃ | CH₂S⁻K⁺ salt | CH₂CF₃ |
| 269 | Pr-i | CF₃ | CH₂S⁻K⁺ salt | CHF₂ |
| 270 | Pr-i | CF₃ | CH₂S⁻K⁺ salt | CH₂CHF₂ |
| 271 | Pr-i | CF₃ | CH₂S⁻K⁺ salt | CH₂CF₃ |
| 272 | Pr-n | CF₃ | CH₂S⁻K⁺ salt | CHF₂ |
| 273 | Pr-n | CF₃ | CH₂S⁻K⁺ salt | CH₂CHF₂ |
| 274 | Pr-n | CF₃ | CH₂S⁻K⁺ salt | CH₂CF₃ |

TABLE 9-continued

| Compound No. | $R^1$ | $R^2$ | $R^3$ | $R^4$ |
|---|---|---|---|---|
| 275 | Bu-n | $CF_3$ | $CH_2S^-K^+$ salt | $CHF_2$ |
| 276 | Bu-n | $CF_3$ | $CH_2S^-K^+$ salt | $CH_2CHF_2$ |
| 277 | Bu-n | $CF_3$ | $CH_2S^-K^+$ salt | $CH_2CF_3$ |

TABLE 10

| Compound No. | $R^1$ | $R^2$ | $R^3$ | $R^4$ |
|---|---|---|---|---|
| 278 | Bu-t | $CF_3$ | $CH_2S^-K^+$ salt | $CHF_2$ |
| 279 | Bu-t | $CF_3$ | $CH_2S^-K^+$ salt | $CH_2CHF_2$ |
| 280 | Bu-t | $CF_3$ | $CH_2S^-K^+$ salt | $CH_2CF_3$ |

TABLE 11

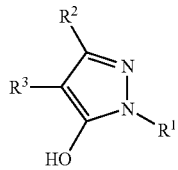

| Compound No. | $R^1$ | $R^2$ | $R^3$ |
|---|---|---|---|
| 281 | Me | $CF_3$ | CHO |
| 282 | Et | $CF_3$ | CHO |
| 283 | Pr-i | $CF_3$ | CHO |
| 284 | Pr-n | $CF_3$ | CHO |
| 285 | Bu-n | $CF_3$ | CHO |
| 286 | Bu-s | $CF_3$ | CHO |
| 287 | Bu-i | $CF_3$ | CHO |
| 288 | Bu-t | $CF_3$ | CHO |
| 289 | Pen-n | $CF_3$ | CHO |
| 290 | Hex-n | $CF_3$ | CHO |
| 291 | Me | $CHF_2$ | CHO |
| 292 | Et | $CHF_2$ | CHO |
| 293 | Pr-i | $CHF_2$ | CHO |
| 294 | Bu-t | $CHF_2$ | CHO |
| 295 | Pen-n | $CHF_2$ | CHO |
| 296 | Hex-n | $CHF_2$ | CHO |

The inventive compounds represented by the general formula [I] can be produced, for example, by the following production processes, but the process for producing the same is not restricted to such processes.

The following will describe each of the production processes in detail.

<Production Process 1>

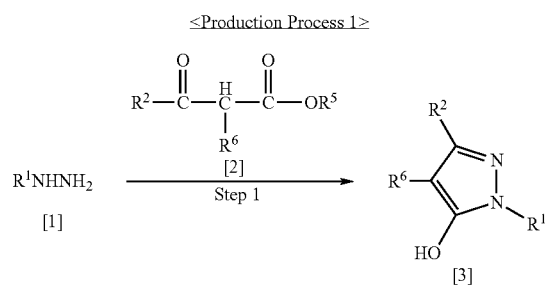

wherein $R^1$ and $R^2$ represent the same meanings as mentioned above, $R^5$ represents a C1 to C3 alkyl group, a phenyl group which may be substituted, or a benzyl group which may be substituted, and $R^6$ is a C1 to C3 alkyl group.

(Step 1)

A compound represented by the general formula [3] can be produced by reacting the compound represented by the general formula [1] with the compound represented by the general formula [2] in a solvent or in the absence of a solvent (preferably in a suitable solvent) in the presence or absence of an acid catalyst.

With respect to the reaction temperature, all the reactions are conducted at any temperature of −50° C. to a reflux temperature of the reaction system, preferably in the temperature range of −20° C. to 100° C. and the reaction may be completed within a period of 0.5 hour to 72 hours, although the period varies depending on the compounds.

With respect to the amounts of the reagents to be used in the reaction, the amount of the compound represented by the general formula [2] is 1 to 3 equivalents and, when an acid catalyst is used, the amount of the acid catalyst when used is 0.01 to 2 equivalents, all relative to 1 equivalent of the compound represented by the general formula [1].

Examples of the solvent include ethers such as dioxane, tetrahydrofuran, and dimethoxyethane; halogenated hydrocarbons such as dichloroethane, carbon tetrachloride, chlorobenzene, and dichlorobenzene; amides such as N,N-dimethylacetamide, N,N-dimethylformamide, and N-methyl-2-pyrrolidinone; sulfur compounds such as dimethyl sulfoxide and sulfolane; aromatic hydrocarbons such as benzene, toluene, and xylene; alcohols such as methanol, ethanol, n-propanol, 2-propanol, n-butanol, and 2-methyl-2-propanol; carboxylic acids such as formic acid and acetic acid; water; and mixtures thereof. The amount of the solvent to be used is in a ratio of 0.1 to 20 liters, preferably 0.1 to 5 liters of the solvent to 1 mol of the compound represented by the general formula [1].

Examples of the acid catalyst include mineral acids such as hydrochloric acid, hydrobromic acid, and sulfuric acid; and organic acids such as formic acid, acetic acid, methanesulfonic acid, and p-toluenesulfonic acid.

<Production Process 2>

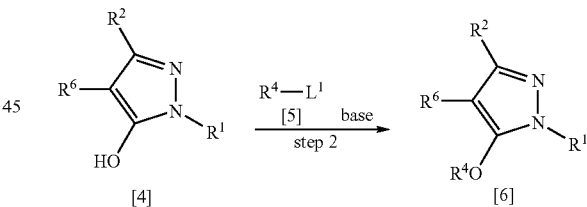

wherein $R^1$, $R^2$, $R^4$, and $R^6$ represent the same meanings as mentioned above, and $L^1$ is a leaving group which is more reactive than a halogen atom remaining after haloalkylation and represents a halogen atom, a C1 to C3 alkylsulfonyloxy group, a C1 to C3 haloalkylsulfonyloxy group, a phenylsulfonyloxy group which may be substituted, a benzylsulfonyloxy group which may be substituted, or the like and, for example, it represents a chlorine atom or a bromine atom when $R^4$ is a $CHF_2$ group and represents a chlorine atom, a bromine atom, an iodine atom, a p-toluenesulfonyloxy group, a trifluoromethanesulfonyloxy group, a methanesulfonyloxy group, or the like when $R^4$ is a $CH_2CF_3$ group.

(Step 2)

A compound represented by the general formula [6] can be produced by reacting the compound represented by the general formula [4] with the compound represented by the general formula [5] in a solvent or in the absence of a solvent (preferably in a suitable solvent) in the presence or absence of a catalyst in the presence of a base.

With respect to the reaction temperature, all the reactions are conducted at any temperature of 0° C. to a reflux temperature of the reaction system, preferably in the temperature range of 0° C. to 100° C. and the reaction may be completed within a period of 0.5 hour to 24 hours, although the period varies depending on the compounds.

With respect to the amounts of the reagents to be used in the reaction, the amount of the compound represented by the general formula [5] is 1 to 5 equivalents, preferably 1 to 3 equivalents, the amount of the base is 1 to 20 equivalents, preferably 1 to 10 equivalents, and the amount of the catalyst is 0.01 to 2.0 equivalents, preferably 0.01 to 0.5 equivalent, all relative to 1 equivalent of the compound represented by the general formula [4].

Examples of the base include alkali metal carbonates such as sodium carbonate and potassium carbonate; alkali metal bicarbonates such as sodium hydrogen carbonate and potassium hydrogen carbonate; alkali metal hydroxides such as sodium hydroxide and potassium hydroxide; alkali metal hydrides such as potassium hydride and sodium hydride; alkali metal alcoholates such as sodium ethoxide and sodium methoxide; and organic bases such as 1,8-diazabicyclo[5.4.0]-7-undecene, triethylamine, and pyridine.

Examples of the solvent include ethers such as dioxane, tetrahydrofuran, and 1,2-dimethoxyethane; halogenated hydrocarbons such as dichloroethane, carbon tetrachloride, chlorobenzene, and dichlorobenzene; amides such as N,N-dimethylacetamide, N,N-dimethylformamide, and N-methyl-2-pyrrolidinone; sulfur compounds such as dimethyl sulfoxide and sulfolane; aromatic hydrocarbons such as benzene, toluene, and xylene; alcohols such as methanol, ethanol, n-propanol, 2-propanol, n-butanol, and 2-methyl-2-propanol; ketones such as acetone and methyl ethyl ketone; nitrites such as acetonitrile; water; and mixtures thereof. The amount of the solvent to be used is in a ratio of 0.1 to 20 liters, preferably 0.1 to 5 liters of the solvent to 1 mol of the compound represented by the general formula [4].

Examples of the catalyst include crown ethers such as 18-crown-6 and 15-crown-5; quaternary ammonium salts such as tetra-n-butylammonium bromide and benzyltrimethylammonium bromide; and quaternary phosphonium salts such as tetra-n-butylphosphoniumm bromide.

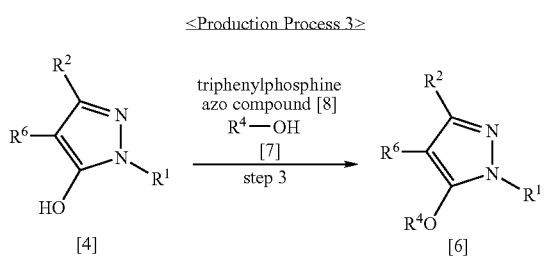

wherein $R^1$, $R^2$, $R^4$, and $R^6$ represent the same meanings as mentioned above.

(Step 3)

A compound represented by the general formula [6] can be produced by reacting the compound represented by the general formula [4] with the compound represented by the general formula [7] in the presence of an azo compound [8] and triphenylphosphine in a solvent, in accordance with the method described in Synthesis, 1981, 1-28.

This reaction is conducted ordinarily at a reaction temperature of −30 to 100° C. for 10 minutes to 24 hours.

With respect to the amounts of the reagents to be used in the reaction, it is desired that the amount of the compound represented by the general formula [7] is 1 to 1.5 equivalents, the amount of the azo compound [8] is 1 to 1.5 equivalents, and the amount of triphenylphosphine is 1 to 1.5 equivalents, all relative to 1 equivalent of the compound represented by the general formula [4], but these amounts can be optionally varied depending upon the conditions of the reaction.

Examples of the solvent include ethers such as dioxane and tetrahydrofuran; halogenated hydrocarbons such as 1,2-dichloroethane, carbon tetrachloride, chlorobenzene, and dichlorobenzene; amides such as N,N-dimethylacetamide, N,N-dimethylformamide, and N-methyl-2-pyrrolidinone; sulfur compounds such as dimethyl sulfoxide and sulfolane; aromatic hydrocarbons such as benzene, toluene, and xylene; nitrites such as acetonitrile; and mixtures thereof. The amount of the solvent to be used is in a ratio of 0.1 to 20 liters, preferably 0.1 to 5 liters of the solvent to 1 mol of the compound represented by the general formula [4].

Examples of the azo compound [8] include diethyl azodicarboxylate, diisopropyl azodicarboxylate, and the like.

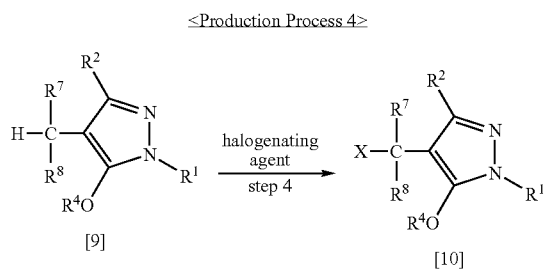

wherein $R^1$, $R^2$, and $R^4$ represent the same meanings as mentioned above, $R^7$ and $R^8$ each represents a hydrogen atom or a C1 to C3 alkyl group, and X is a halogen atom.

(Step 4)

The compound represented by the general formula [10] can be produced by reacting the compound represented by the general formula [9] with a halogenating agent in a solvent in the presence or absence of a catalyst. In this step, the reaction may be conducted under light irradiation. Furthermore, in order to trap an acid produced as a by-product, the reaction may be conducted in the presence of a base.

This reaction is conducted ordinarily at a reaction temperature of 20 to 150° C. for 10 minutes to 48 hours.

With respect to the amounts of the reagents to be used, the amount of the halogenating agent is desirably 1 to 10 equivalents relative to 1 equivalent of the compound of the general formula [9] but it can be optionally varied depending upon the conditions of the reaction. The amount of the catalyst is 0.01 to 3.0 equivalent, preferably 0.01 to 1.5 equivalents.

Examples of the halogenating agent include halogens such as bromine and chlorine; N-halosuccinimides such as N-bromosuccinimide and N-chlorosuccinimide; pyridine salts such as pyridinium perbromide; sulfuryl chloride, 1,3-dibromo-5,5-dimethylhydantoin, and the like.

Examples of the solvent include halogenated hydrocarbons such as 1,2-dichloroethane, carbon tetrachloride, chlorobenzene, fluorobenzen and dichlorobenzene; benzene; carboxylic acids such as formic acid and acetic acid; water; and mixtures thereof. The amount of the solvent to be used is in a ratio of 0.1 to 20 liters, preferably 0.1 to 5 liters of the solvent to 1 mol of the compound represented by the general formula [9].

Examples of the catalyst include benzoyl peroxide, a hydrogen peroxide solution, α,α'-azobisisobutyronitrile, and mixtures thereof.

Examples of the base include alkali metal hydroxides such as sodium hydroxide and potassium hydroxide; alkali metal carbonates such as sodium carbonate and potassium carbonate; alkali metal bicarbonates such as sodium hydrogen carbonate and potassium hydrogen carbonate; and the like.

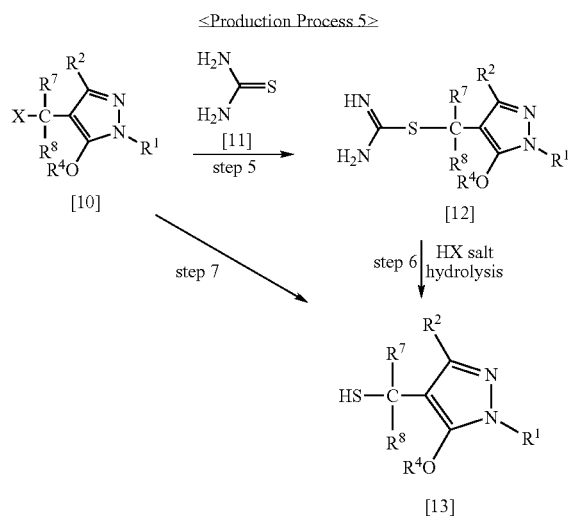

wherein $R^1$, $R^2$, $R^4$, $R^7$, $R^8$, and X represent the same meanings as mentioned above.

(Step 5)

The compound represented by the general formula [12] can be produced by reacting the compound represented by the general formula [10] with the compound represented by the general formula [11] (thiourea) in a solvent.

With respect to the amounts of the reagents to be used, the amount of the a compound represented by the general formula [11] is desirably 1 to 1.5 equivalents relative to 1 equivalent of the compound of the general formula [10], but it can be optionally varied depending upon the conditions of the reaction.

Examples of the solvent include ethers such as dioxane and tetrahydrofuran; halogenated hydrocarbons such as dichloroethane, carbon tetrachloride, chlorobenzene, and dichlorobenzene; aromatic hydrocarbons such as benzene, toluene, and xylene; amides such as N,N-dimethylacetamide, N,N-dimethylformamide, and N-methyl-2-pyrrolidinone; alcohols such as methanol, ethanol, and 2-propanol; nitrites such as acetonitrile; ketones such as acetone and methyl ethyl ketone; water; and mixtures thereof. The amount of the solvent to be used is in a ratio of 0.1 to 20 liters, preferably 0.1 to 5 liters of the solvent to 1 mol of the compound represented by the general formula [10].

(Step 6)

The compound represented by the general formula [13] can be produced by hydrolyzing a compound represented by the general formula [12] in a solvent in the presence or absence of a base. In this step, the compound may be produced in the presence or absence of a reducing agent or under an inert gas stream. Moreover, the compound represented by the general formula [13] may be used in the next reaction without isolation and purification.

With respect to the amounts of the reagents to be used, the amount of the base is desirably 1 to 10 equivalents relative to 1 equivalent of the compound of the general formula [12], but it can be optionally varied depending upon the conditions of the reaction.

Examples of the solvent include ethers such as dioxane and tetrahydrofuran; halogenated hydrocarbons such as dichloroethane, carbon tetrachloride, chlorobenzene, and dichlorobenzene; aromatic hydrocarbons such as benzene, toluene, and xylene; amides such as N,N-dimethylacetamide, N,N-dimethylformamide, and N-methyl-2-pyrrolidinone; sulfur compounds such as dimethyl sulfoxide and sulfolane; aromatic hydrocarbons such as benzene, toluene, and xylene; nitriles such as acetonitrile; alcohols such as methanol, ethanol, and 2-propanol; ketones such as acetone and methyl ethyl ketone; water; and mixtures thereof. The amount of the solvent to be used is in a ratio of 0.1 to 20 liters, preferably 0.1 to 5 liters of the solvent to 1 mol of the compound represented by the general formula [12].

Examples of the base include alkali metal carbonates such as sodium carbonate and potassium carbonate; alkali metal hydroxides such as sodium hydroxide and potassium hydroxide; alkali metal bicarbonates such as sodium hydrogen carbonate and potassium hydrogen carbonate; alkali metal alcoholates such as sodium ethoxide and sodium methoxide; and organic bases such as 1,8-diazabicyclo[5.4.0]-7-undecene.

Examples of the reducing agent include sodium borohydride and the like.

Examples of the inert gas include nitrogen, argon, and the like.

(Step 7)

The compound represented by the general formula [13] can be produced by reacting the compound represented by the general formula [10] with a sulfide in a solvent in the presence or absence of a base. In this step, the compound may be produced in the presence or absence of a reducing agent or under an inert gas stream. Moreover, the compound represented by the general formula [13] may be used in the next reaction without isolation and purification.

With respect to the amounts of the reagents to be used, it is desirable that the amount of the sulfide is 1 to 5 equivalents and the amount of the base is 1 to 10 equivalents, all relative to 1 equivalent of the compound of the general formula [10], but these can be optionally varied depending upon the conditions of the reaction.

Examples of the solvent include ethers such as dioxane and tetrahydrofuran; halogenated hydrocarbons such as dichloroethane, carbon tetrachloride, chlorobenzene, and dichlorobenzene; aromatic hydrocarbons such as benzene, toluene, and xylene; amides such as N,N-dimethylacetamide, N,N-dimethylformamide, and N-methyl-2-pyrrolidinone; sulfur compounds such as dimethyl sulfoxide and sulfolane; aromatic hydrocarbons such as benzene, toluene, and xylene; nitrites such as acetonitrile; alcohols such as methanol, ethanol, and 2-propanol; ketones such as acetone and methyl ethyl ketone; water; and mixtures thereof. The amount of the solvent to be used is in a ratio of 0.1 to 20 liters, preferably 0.1 to 5 liters of the solvent to 1 mol of the compound represented by the general formula [10].

Examples of the sulfide include alkali metal sulfides such as sodium sulfide and potassium sulfide; alkali metal hydrosulfides such as sodium hydrosulfide and potassium hydrosulfide; hydrogen sulfide, ammonium sulfide, sodium thioacetate, potassium thioacetate, and the like.

Examples of the base include alkali metal carbonates such as sodium carbonate and potassium carbonate; alkali metal hydroxides such as sodium hydroxide and potassium hydroxide; alkali metal hydrides such as potassium hydride and sodium hydride; alkali metal alcoholates such as sodium ethoxide and sodium methoxide; and organic bases such as 1,8-diazabicyclo[5.4.0]-7-undecene.

As the reducing agent and the inert gas, those the same as in Step 6 of Production Process 5 may be mentioned.

<Production Process 6>

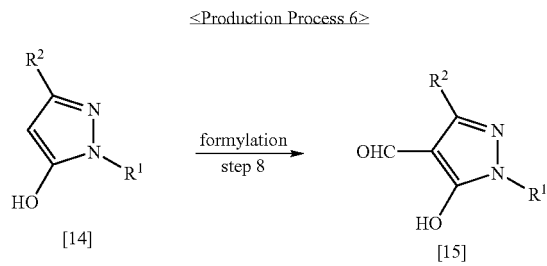

wherein $R^1$ and $R^2$ represent the same meanings as mentioned above.

(Step 8)

The compound represented by the general formula [15] can be produced by reacting the compound of the general formula [14] with N,N-dimethylformamide in a solvent or in the absence of a solvent in the presence of phosphoryl chloride, phosgene, or thionyl chloride in accordance with the Vilsmeier method described in Org. Synth., Vol. IV, 831 (1963), or by reacting the compound of the general formula [14] with a dihalogenomethyl ether in a solvent in the presence of a Lewis acid, followed by hydrolysis, in accordance with the method described in Chem. Ber., 93, 88 (1960).

This reaction is conducted ordinarily at −40 to 150° C. for 10 minutes to 24 hours.

With respect to the amounts of reagents to be used in the reaction, it is desired that the amount of phosphoryl chloride, phosgene, thionyl chloride, N,N-dimethylformamide, Lewis acid, or dihalogenomethyl ether is 1 to 1.5 equivalents, relative to 1 equivalent of the compound of the general formula [14], but the amount can be optionally varied depending upon the conditions of the reaction.

Examples of the Lewis acid include titanium tetrachloride, tin tetrachloride, zinc chloride, aluminum chloride, zinc bromide, and the like.

Examples of the dihalogenomethyl ether include dichloromethyl methyl ether and the like.

Examples of the solvent include halogenated hydrocarbons such as dichloroethane, carbon tetrachloride, and chloroform; aliphatic hydrocarbons such as hexane and heptane; ethers such as dioxane and tetrahydrofuran; carboxylic acids such as acetic acid; amides such as N,N-dimethylformamide; carbon disulfide; and mixtures thereof. The amount of the solvent to be used is in a ratio of 0.1 to 20 liters, preferably 0.2 to 5 liters of the solvent to 1 mol of the compound represented by the general formula [14].

<Production Process 7>

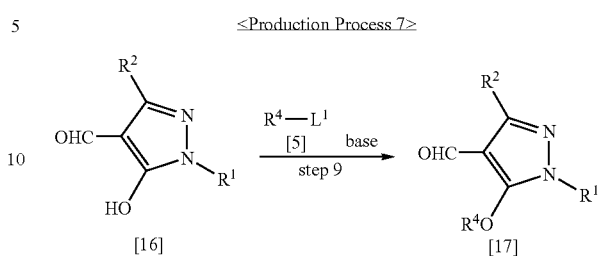

wherein $R^1$, $R^2$, $R^4$, and $L^1$ represent the same meanings as mentioned above.

(Step 9)

The compound represented by the general formula [17] can be produced by reacting the compound represented by the general formula [16] with the compound represented by the general formula [5] in a solvent or in the absence of a solvent (preferably in a suitable solvent) in the presence or absence of a catalyst in the presence of a base.

With respect to the reaction temperature, all the reactions are carried out at any temperature of 0° C. to a reflux temperature of the reaction system, preferably in the temperature range of 0° C. to 100° C. and the reaction may be conducted for 0.5 hour to 24 hours, although the period varies depending on the compounds.

With respect to the amounts of the reagents to be used in the reaction, the amount of the compound represented by the general formula [5] is 1 to 5 equivalents, preferably 1 to 3 equivalents, the amount of the base is 1 to 20 equivalents, preferably 1 to 10 equivalents, and the amount of the catalyst is 0.01 to 2.0 equivalents, preferably 0.01 to 0.5 equivalent, all relative to 1 equivalent of the compound represented by the general formula [16].

As the solvent, the base, and the catalyst, those the same as in Step 2 of Production Process 2 may be mentioned.

<Production Process 8>

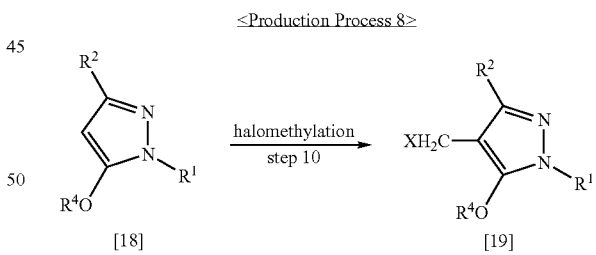

wherein $R^1$, $R^2$, $R^4$, and X represent the same meanings as mentioned above.

(Step 10)

The compound represented by the general formula [19] can be produced by reacting the compound represented by the general formula [18] with a hydrogen halide and formaldehyde or paraformaldehyde in a solvent in the presence or absence of a Lewis acid, in accordance with the method described in Org. Synth., Vol. III, 557 (1955) or J. Amer. Chem. Soc., 72, 2216 (1950), or by reacting the compound represented by the general formula [18] with a halogenomethyl ether in a solvent or without solvent in the presence of a Lewis acid, in accordance with the method described in J. Amer. Chem. Soc., 97, 6155 (1975).

This reaction is conducted ordinarily at −40 to 150° C. for 10 minutes to 24 hours.

With respect to the amounts of the reagents used, it is desired that the amount of the hydrogen halide is 1 to 2 equivalents, the amount of formaldehyde or paraformaldehyde is 1 to 2 equivalents, the amount of the Lewis acid is 1 to 2 equivalents, and the amount of the halogenomethyl ether is 1 to 2 equivalents, all relative to 1 equivalent of the compound of the general formula [18]. However, these amounts can be optionally varied depending upon the conditions of the reaction.

Examples of the Lewis acid include titanium tetrachloride, zinc chloride, aluminum chloride, zinc bromide, and the like.

Examples of the hydrogen halide include hydrogen chloride, hydrogen bromide, and hydrogen iodide.

Examples of the halogenomethyl ether include chloromethyl methyl ether, bromomethyl methyl ether, and the like.

Examples of the solvent include halogenated hydrocarbons such as dichloroethane, carbon tetrachloride, and chloroform; aliphatic hydrocarbons such as hexane and heptane; ethers such as dioxane and tetrahydrofuran; carboxylic acids such as acetic acid; carbon disulfide; and mixtures thereof. The amount of the solvent to be used is in a ratio of 0.1 to 20 liters, preferably 0.1 to 5 liters of the solvent to 1 mol of the compound represented by the general formula [18].

In this connection, the compound represented by the general formula [18] can be produced by converting the hydrogen atom of the corresponding compound wherein $R^4$ is a hydrogen atom into the $R^4$ in accordance with Production Process 2 or 3.

The following will explain the processes for producing the inventive compounds specifically. Also, physical properties of the inventive compounds produced in respective Examples or produced in accordance with respective Examples are shown.

EXAMPLE 1

Production of 1-tert-butyl-5-difluoromethoxy-3-trifluoromethyl-1H-pyrazole (Inventive Compound No. 021)

To a solution of 10.4 g (50.0 mmol) of 1-tert-butyl-5-hydroxy-3-trifluoromethyl-1H-pyrazole in 50 ml of N,N-dimethylformamide was added 7.6 g (55.0 mmol) of anhydrous potassium carbonate at room temperature. While the reaction solution was stirred, an excess amount of chlorodifluoromethane was introduced into the reaction solution at 80° C. After the confirmation of disappearance of the starting material, the introduction of chlorodifluoromethane was stopped and the reaction solution was cooled to room temperature. Thereafter, the reaction solution was poured into water and extracted with diisopropyl ether. The resulting organic layer was washed with water and dried over anhydrous magnesium sulfate. The solvent was removed by evaporation under reduced pressure and the residue was distilled under reduced pressure to obtain 10.8 g (yield: 83.7%) of 1-tert-butyl-5-difluoromethoxy-3-trifluoromethyl-1H-pyrazole as a yellow liquid.

$^1$H-NMR value (CDCl$_3$/TMS δ (ppm)): 6.53(1H, t, J=71.9 Hz), 6.14(1H, s), 1.63(9H, s)

EXAMPLE 2

Production of 1-tert-butyl-5-(2,2-difluoroethoxy)-3-trifluoromethyl-1H-pyrazole (Inventive Compound No. 022)

To a solution of 50.0 g (240.2 mmol) of 1-tert-butyl-5-hydroxy-3-trifluoromethyl-1H-pyrazole in 1000 ml of tetrahydrofuran were added 75.6 g (288.2 mmol) of triphenylphosphine and 23.7 g (288.8 mmol) of 2,2-difluoroethanol at room temperature, followed by stirring. Under ice-cooling, 58.3 g (288.3 mmol) of diisopropyl azodicarboxylate was added into the reaction solution, followed by 5 hours of stirring. After the completion of the reaction was confirmed, the reaction solution was poured into water and extracted with diethyl ether. The resulting organic layer was washed with water and dried over anhydrous magnesium sulfate. The solvent was removed by evaporation under reduced pressure and the residue was distilled under reduced pressure to obtain 38.2 g (yield: 58.4%) of 1-tert-butyl-5-(2,2-difluoroethoxy)-3-trifluoromethyl-1H-pyrazole.

Boiling point: 98 to 100° C./6 KPa (45 mmHg) Refractive index ($n^D_{20}$): 1.3921 $^1$H-NMR value (CDCl$_3$/TMS δ (ppm)): 6.10(1H, tt, J=3.8, 54.5 Hz), 5.84(1H, s), 4.25(2H, dt, J=3.8, 13.0 Hz), 1.60(9H, s)

EXAMPLE 3

Production of 1-tert-butyl-4-chloromethyl-5-(2,2-difluoroethoxy)-3-trifluoromethyl-1H-pyrazole (Inventive Compound No. 141)

To a solution of 13.6 g (50.0 mmol) of 1-tert-butyl-5-(2,2-difluoroethoxy)-3-trifluoromethyl-1H-pyrazole in 50 ml of acetic acid were added 5.0 g (purity: 90%, 150.0 mmol) of paraformaldehyde and 20.5 g (150.0 mmol) of zinc chloride at room temperature, followed by stirring. Furthermore, an excess amount of hydrogen chloride was introduced into the reaction solution under ice-cooling, followed by 1 hour of stirring. After the completion of the reaction was confirmed, the reaction solution was poured into water and extracted with diethyl ether. The resulting organic layer was washed with water and dried over anhydrous magnesium sulfate. The solvent was removed by evaporation under reduced pressure and a gas chromatographic analysis was conducted to confirm that 1-tert-butyl-4-chloromethyl-5-(2,2-difluoroethoxy)-3-trifluoromethyl-1H-pyrazole was formed in an amount of 50.1%.

EXAMPLE 4

Production of 5-hydroxy-1-methyl-3-trifluoromethyl-1H-pyrazole-4-carbaldehyde (Inventive Compound No. 281)

Into 16.6 g (100.0 mmol) of 5-hydroxy-1-methyl-3-trifluoromethyl-1H-pyrazole in 15.4 g of N,N-dimethylformaldehyde was added 16.2 g (105.0 mmol) of phosphorus oxychloride at 0° C., followed by 1 hour of stirring at room temperature. Furthermore, the whole was stirred at 100° C. for 1 hour. After the completion of the reaction was confirmed, the reaction solution was poured into water and the pH was made 10 or more with a 25% sodium hydroxide solution and then the aqueous layer was washed with ethyl acetate. The pH of the resulting aqueous layer was made about 4 with a saturated citric acid solution and then extracted with diethyl ether. The resulting organic layer was washed with water and saline, successively, and then dried over anhydrous magnesium sulfate. The solvent was removed by evaporation under reduced pressure and the residue was purified by silica gel column chromatography to obtain 4.5 g (yield: 23.2%) of 5-hydroxy-1-methyl-3-trifluoromethyl-1H-pyrazole-4-carbaldehyde.

EXAMPLE 5

Production of 5-difluoromethoxy-1-methyl-3-trifluoromethyl-1H-pyrazole-4-carbaldehyde (Inventive Compound No. 026)

To 1.7 g (8.8 mmol) of 5-hydroxy-1-methyl-3-trifluoromethyl-1H-pyrazole in 20 ml of tetrahydrofuran were added 2.5 g (43.8 mmol) of powdery potassium hydroxide and 0.14 g (0.44 mmol) of tetrabutylammonium bromide at room temperature, followed by stirring. Furthermore, chlorodifluoromethane was introduced into the reaction solution until the reaction system was saturated therewith. Thereafter, the whole was stirred at room temperature overnight. After the completion of the reaction was confirmed, the reaction solution was poured into water and extracted with diethyl ether. The resulting organic layer was washed with water and saline, successively, and then dried over anhydrous magnesium sulfate. The solvent was removed by evaporation under reduced pressure and a gas chromatographic analysis was conducted to confirm that 5-difluoromethoxy-1-methyl-3-trifluoromethyl-1H-pyrazole-4-carbaldehyde was formed in an amount of 8.8%.

EXAMPLE 6

Production of 1,4-dimethyl-5-hydroxy-3-trifluoromethyl-1H-pyrazole (Inventive Compound No. 036)

To a solution of 20.9 g (454.2 mmol) of methylhydrazine in 500 ml of ethanol was added dropwise under stirring 90.0 g (454.2 mmol) of ethyl 4,4,4-trifluoro-2-methyl-3-oxobutanoate under ice-cooling so that the temperature did not exceed 10° C. After the completion of the dropwise addition, the whole was stirred at room temperature for 30 minutes. Then, 10 ml of concentrated hydrochloric acid was added into the reaction solution, followed by 2 days of stirring under refluxing. After the completion of the reaction was confirmed, the solvent was removed by evaporation under reduced pressure. Water was added to the residue, followed by extraction with ethyl acetate. The resulting organic layer was washed with water and saline, successively, and then dried over anhydrous magnesium sulfate. The solvent was removed by evaporation under reduced pressure and the residue was washed with n-hexane to obtain 61.0 g (yield: 74.6%) of 1,4-dimethyl-5-hydroxy-3-trifluoromethyl-1H-pyrazole as white crystals (melting point: 148 to 151° C.).

$^1$H-NMR value (CDCl$_3$/TMS δ (ppm)): 3.70(3H, d), 1.99(3H, d) Melting point: 148 to 151° C.

EXAMPLE 7

Production of 5-difluoromethoxy-1,4-dimethyl-3-trifluoromethyl-1H-pyrazole (Inventive Compound No. 076)

Into 78.6 g (436.4 mmol) of 1,4-dimethyl-5-hydroxy-3-trifluoromethyl-1H-pyrazole in 500 ml of 2-propanol was added 153.1 g (2728.6 mmol) of powdery potassium hydroxide at room temperature, followed by stirring. Furthermore, an excess amount of chlorodifluoromethane was introduced into the reaction solution under stirring. Thereafter, the reaction temperature once rose to 70° C. by exothermic heat and then returned to room temperature after 2 hours. After the completion of the reaction was confirmed, the reaction solution was poured into water and extracted with ethyl acetate. The resulting organic layer was washed with water and saline, successively, and then dried over anhydrous magnesium sulfate. The solvent was removed by evaporation under reduced pressure and the residue was distilled to obtain 88.9 g (yield: 88.5%) of 5-difluoromethoxy-1,4-dimethyl-3-trifluoromethyl-1H-pyrazole as a colorless transparent liquid.

$^1$H-NMR value (CDCl$_3$/TMS δ (ppm)): 6.52(1H, t, J=71.5 Hz), 3.78(3H, s), 2.07(3H, s) Boiling point: 98 to 100° C./6 KPa (45 mmHg) Refractive index ($n^D_{20}$): 1.3921

EXAMPLE 8

Production of 4-bromomethyl-5-difluoromethoxy-1-methyl-3-trifluoromethyl-1H-pyrazole (Inventive Compound No. 151)

To a solution of 11.5 g (50.0 mmol) of 5-difluoromethoxy-1,4-dimethyl-3-trifluoromethyl-1H-pyrazole in 50 ml of carbon tetrachloride were added 9.8 g (55.0 mmol) of N-bromosuccinimide and 0.41 (2.5 mmol) of α,α'-azobisisobutyronitrile, followed by heating and refluxing under stirring. The reaction solution was externally irradiated with a light for 1 hour. After the completion of the reaction was confirmed, the reaction solution was poured into water and extracted with chloroform. The resulting organic layer was washed with water and saline, successively, and then dried over anhydrous magnesium sulfate. The solvent was removed by evaporation under reduced pressure to obtain 17.8 g (purity: 72.0%, yield: 82.7%) of 4-bromomethyl-5-difluoromethoxy-1-methyl-3-trifluoromethyl-1H-pyrazole.

$^1$H-NMR value (CDCl$_3$/TMS δ (ppm)): 6.73(1H, t, J=71.5 Hz), 4.39(2H, s), 3.82(3H, d) Refractive index ($n^D_{20}$): 1.4401

EXAMPLE 9

Production of 4-bromomethyl-5-difluoromethoxy-1-methyl-3-trifluoromethyl-1H-pyrazole (Inventive Compound No. 151)

To a solution of 0.50 g (2.17 mmol) of 5-difluoromethoxy-1,4-dimethyl-3-trifluoromethyl-1H-pyrazole in 5 ml of carbon tetrachloride were added 0.90 g (5.64 mmol) of bromine and a minute amount of benzoyl peroxide, followed by heating and refluxing under stirring. The reaction solution was externally irradiated with a light for 2 hours and 30 minutes. After the completion of the reaction, a gas chromatographic analysis was conducted to confirm that 4-bromomethyl-5-difluoromethoxy-1-methyl-3-trifluoromethyl-1H-pyrazole was formed in an amount of 80.2%.

EXAMPLE 10

Production of 2-(5-difluoromethoxy-1-methyl-3-trifluoromethyl-1H-pyrazole-4-ylmethyl)-isothiourea hydrobromide (Inventive Compound No. 197)

To a solution of 19.1 g (purity: 75.0%, 46.3 mmol) of 4-bromomethyl-5-difluoromethoxy-1-methyl-3-trifluoromethyl-1H-pyrazole in 30 ml of ethanol was added 3.5 g (46.3 mmol) of thiourea, followed by 1 hour of heating and refluxing under stirring. The solvent was removed by evaporation under reduced pressure and the residue was washed with a mixed solvent of ethyl acetate and n-hexane to obtain 13.8 g (yield: 77.5%) of 2-(5-difluoromethoxy-1-methyl-3-trifluoromethyl-1H-pyrazole-4-ylmethyl)-isothiourea hydrobromide as white crystals (melting point: 130 to 131° C.).

$^1$H-NMR value (CDCl$_3$+DMSO-d6/TMS δ (ppm)): 9.21 (2H, br), 9.12(2H, br), 6.92(1H, t, J=71.2 Hz), 4.40(2H, s), 3.83(3H, s)

EXAMPLE 11

Production of (5-difluoromethoxy-1-methyl-3-trifluoromethyl-1H-pyrazole-4-yl)-methanethiol(Inventive Compound No. 216)

To a solution of 1.00 g (2.60 mmol) of 2-(5-difluoromethoxy-1-methyl-3-trifluoromethyl-1H-pyrazole-4-ylmethyl)-isothiourea hydrobromide in 2 ml of N,N-dimethylformamide were added 0.43 g (3.12 mmol) of anhydrous potassium carbonate and 1 ml of water, followed by 1 hour of stirring at room temperature. After the completion of the reaction was confirmed, the reaction solution was poured into water and extracted with diethyl ether. The resulting organic layer was washed with water and then dried over anhydrous magnesium sulfate. The solvent was removed by evaporation under reduced pressure to obtain 0.66 g (purity: 84.9%, yield: 82.4%) of (5-difluoromethoxy-1-methyl-3-trifluoromethyl-1H-pyrazole-4-yl)-methanethiol.

$^1$H-NMR value (CDCl$_3$/TMS δ (ppm)): 6.72(1H, t, J=71.7 Hz), 3.81 (3H, s), 3.63(2H, s), 3.20(1H, br)

EXAMPLE 12

Production of (5-difluoromethoxy-1-methyl-3-trifluoromethyl-1H-pyrazole-4-yl)-methanethiol (Inventive Compound No. 216)

To a solution of 1.55 g (5.00 mmol) of 4-bromomethyl-5-difluoromethoxy-1-methyl-3-trifluoromethyl-1H-pyrazole in 10 ml of ethanol was added 0.48 g (purity: 70.0%, 6.00 mmol) of sodium hydrosulfide n.hydrate, followed by 1 hour of stirring at room temperature. After the completion of the reaction, a gas chromatographic analysis was conducted to confirm that (5-difluoromethoxy-1-methyl-3-trifluoromethyl-1H-pyrazole-4-yl)-methanethiol was formed in an amount of 40.0%.

EXAMPLE 13

Production of 4-chloromethyl-5-difluoromethoxy-1-methyl-3-trifluoromethyl-1H-pyrazole (Inventive Compound No. 123)

To a solution of 11.5 g (50.0 mmol) of 5-difluoromethoxy-1,4-dimethyl-3-trifluoromethyl-1H-pyrazole in 50 ml of carbon tetrachloride were added 10.1 g (75.0 mmol) of sulfuryl chloride and 0.8 (5.0 mmol) of α,α'-azobisisobutyronitrile, followed by heating and refluxing under stirring. The reaction solution was externally irradiated with a light for 11 hours. After the completion of the reaction was confirmed, the reaction solution was poured into water and extracted with chloroform. The resulting organic layer was washed with water and saline, successively, and then dried over anhydrous magnesium sulfate. The solvent was removed by evaporation under reduced pressure and the residue was purified by silica gel column chromatography to obtain 4.8 g (purity: 83.4%, yield: 30.3%) of 4-chloromethyl-5-difluoromethoxy-1-methyl-3-trifluoromethyl-1H-pyrazole as a colorless transparent liquid.

$^1$H-NMR value (CDCl$_3$/TMS δ (ppm)): 6.69(1H, t, J=71.5 Hz), 4.51(2H, s), 3.82(3H, s) Refractive index ($n^D_{20}$): 1.4157

EXAMPLE 14

Production of 4-chloromethyl-5-difluoromethoxy-1-methyl-3-trifluoromethyl-1H-pyrazole (Inventive Compound No. 123)

To a solution of 1.00 g (4.35 mmol) of 5-difluoromethoxy-1,4-dimethyl-3-trifluoromethyl-1H-pyrazole in 10 ml of carbon tetrachloride was added 0.55 g (6.52 mmol) of sodium hydrogen carbonate, followed by heating and refluxing under stirring. The reaction solution was externally irradiated with a light and chlorine gas was introduced in a suitable amount while the amount of the aimed compound formed was confirmed by gas chromatography. After the completion of the reaction, a gas chromatographic analysis was conducted to confirm that 4-chloromethyl-5-difluoromethoxy-1-methyl-3-trifluoromethyl-1H-pyrazole was formed in an amount of 61.7%.

EXAMPLE 15

Production of 2-(5-difluoromethoxy-1-methyl-3-trifluoromethyl-1H-pyrazole-4-ylmethyl)-isothiourea hydrochloride (Inventive Compound No. 178)

To a solution of 3.7 g (purity: 83.4%, 11.7 mmol) of 4-chloromethyl-5-difluoromethoxy-1-methyl-3-trifluoromethyl-1H-pyrazole in 20 ml of ethanol was added 0.8 g (11.1 mmol) of thiourea, followed by stirring at room temperature overnight and further heating and stirring at 50° C. for 1 hour. The solvent was removed by evaporation under reduced pressure and the residue was washed with n-hexane to obtain 3.8 g (yield: 96.4%) of 2-(5-difluoromethoxy-1-methyl-3-trifluoromethyl-1H-pyrazole-4-ylmethyl)-isothiourea hydrochloride as white crystals (melting point: 117 to 119° C.)

EXAMPLE 16

Production of 1-ethyl-5-hydroxy-4-methyl-3-trifluoromethyl-1H-pyrazole (Inventive Compound No. 037)

To a solution of 1.2 g (20.0 mmol) of ethylhydrazine in 20 ml of ethanol was added dropwise under stirring 4.4 g (20.0 mmol) of ethyl 4,4,4-trifluoro-2-methyl-3-oxobutanoate under ice-cooling so that the temperature in the reaction system did not exceed 10° C. After the dropwise addition, the whole was stirred at room temperature for 30 minutes. Then, 1 ml of concentrated hydrochloric acid was added into the reaction solution, followed by 2 days of stirring under refluxing. After the completion of the reaction was confirmed, the solvent was removed by evaporation under reduced pressure. Water was added to the residue, followed by extraction with ethyl acetate. The resulting organic layer was washed with water and saline, successively, and then dried over anhydrous magnesium sulfate. The solvent was removed by evaporation under reduced pressure and the residue was washed with n-hexane to obtain 2.8 g (yield: 71.8%) of 1-ethyl-5-hydroxy-4-methyl-3-trifluoromethyl-1H-pyrazole as white crystals (melting point: 150 to 152° C.).

$^1$H-NMR value (CDCl$_3$/TMS δ (ppm)): 6.78(1H, br), 4.06(2H, q), 1.98(3H, d), 1.37(3H, t)

EXAMPLE 17

Production of 5-hydroxy-4-methyl-1-iso-propyl-3-trifluoromethyl-1H-pyrazole (Inventive Compound No. 038)

To a solution of 7.4 g (100.0 mmol) of isopropylhydrazine in 100 ml of ethanol was added dropwise under stirring 23.3 g (purity: 85.0%, 100.0 mmol) of ethyl 4,4,4-trifluoro-2-methyl-3-oxobutanoate under ice-cooling so that the temperature in the reaction system did not exceed 10° C. After the dropwise addition, the whole was stirred at room temperature for 30 minutes. Then, 1 ml of concentrated hydrochloric acid was added into the reaction solution, followed by 2 days of stirring under refluxing. After the completion of the reaction was confirmed, the solvent was removed by evaporation under reduced pressure. Water was added to the residue, followed by extraction with ethyl acetate. The resulting organic layer was washed with water and saline, successively, and then dried over anhydrous magnesium sulfate. The solvent was removed by evaporation under reduced pressure and the residue was washed with n-hexane to obtain 18.1 g (yield: 87.0%) of 5-hydroxy-4-methyl-1-iso-propyl-3-trifluoromethyl-1H-pyrazole as white crystals (melting point: 150 to 153° C.).

$^1$H-NMR value (CDCl$_3$/TMS δ (ppm)): 4.58(1H, m), 1.98(3H, d), 1.44(6H, d)

EXAMPLE 18

Production of 5-difluoromethoxy-4-methyl-1-iso-propyl-3-trifluoromethyl-1H-pyrazole (Inventive Compound No. 084)

Into 17.1 g (82.1 mmol) of 5-hydroxy-4-methyl-1-iso-propyl-3-trifluoromethyl-1H-pyrazole in 100 ml of 2-propanol was added 23.0 g (410.7 mmol) of powdery potassium hydroxide at room temperature, followed stirring. Furthermore, stirring was continued while an excess amount of chlorodifluoromethane was introduced into the reaction solution. Thereafter, the reaction temperature once rose to 70° C. by exothermic heat and then returned to room temperature after 2 hours. After the completion of the reaction was confirmed, the reaction solution was poured into water and extracted with ethyl acetate. The resulting organic layer was washed with water and saline, successively, and then dried over anhydrous magnesium sulfate. The solvent was removed by evaporation under reduced pressure and the residue was distilled to obtain 15.9 g (yield: 75.0%) of 5-difluoromethoxy-4-methyl-1-iso-propyl-3-trifluoromethyl-1H-pyrazole as a colorless transparent liquid.

$^1$H-NMR value (CDCl$_3$/TMS δ (ppm)): 6.52(1H, t, J=71.5 Hz), 4.58(1H, m), 1.98(3H, d), 1.44(6H, d) Boiling point: 84 to 86° C./3.33 KPa (25 mmHg) Refractive index (n$^D_{20}$): 1.3974

EXAMPLE 19

Production of 4-bromomethyl-5-difluoromethoxy-1-iso-propyl-3-trifluoromethyl-1H-pyrazole (Inventive Compound No. 158)

To a solution of 10.3 g (40.0 mmol) of 5-difluoromethoxy-4-methyl-1-iso-propyl-3-trifluoromethyl-1H-pyrazole in 40 ml of carbon tetrachloride were added 7.8 g (44.0 mmol) of N-bromosuccinimide and 0.3 (2.0 mmol) of α,α'-azobisisobutyronitrile, followed by heating and refluxing under stirring. The reaction solution was externally irradiated with a light for 1 hour. After the completion of the reaction was confirmed, the reaction solution was poured into water and extracted with chloroform. The resulting organic layer was washed with water and saline, successively, and then dried over anhydrous magnesium sulfate. The solvent was removed by evaporation under reduced pressure and the residue was purified by silica gel column chromatography to obtain 5.5 g (yield: 40.7%) of 4-bromomethyl-5-difluoromethoxy-1-iso-propyl-3-trifluoromethyl-1H-pyrazole.

$^1$H-NMR value (CDCl$_3$/TMS δ (ppm)): 6.72(1H, t, J=71.9 Hz), 4.62(1H, m), 4.40(2H, s), 1.47(6H, d, J=6.8 Hz) Refractive index (n$^D_{20}$): 1.4383

EXAMPLE 20

Production of 1,4-dimethyl-5-(2,2,2-trifluoroethoxy)-3-trifluoromethyl-1H-pyrazole (Inventive Compound No. 079)

To a solution of 4.4 g (24.4 mmol) of 1,4-dimethyl-5-hydroxy-3-trifluoromethyl-1H-pyrazole in 50 ml of N,N-dimethylformamide were added 5.1 g (36.6 mmol) of anhydrous potassium carbonate and 6.3 (26.8 mmol) of 2,2,2-trifluoroethyl trifluoromethanesulfonate, followed by 3 hours of stirring at room temperature. After the completion of the reaction was confirmed, the reaction solution was poured into water and extracted with ethyl acetate. The resulting organic layer was washed with water and saline, successively, and then dried over anhydrous magnesium sulfate. The solvent was removed by evaporation under reduced pressure to obtain 6.1 g (yield: 95.3%) of 1,4-dimethyl-5-(2,2,2-trifluoroethoxy)-3-trifluoromethyl-1H-pyrazole as a pale yellow liquid.

$^1$H-NMR value (CDCl$_3$/TMS δ (ppm)): 4.41(2H, q), 3.74(3H, d), 2.08(3H, d) Refractive index (n$^D_{20}$): 1.3872

EXAMPLE 21

Production of 5-(2,2-difluoroethoxy)-1,4-dimethyl-3-trifluoromethyl-1H-pyrazole (Inventive Compound No. 078)

To a solution of 9.0 g (50.0 mmol) of 1,4-dimethyl-5-hydroxy-3-trifluoromethyl-1H-pyrazole in 50 ml of tetrahydrofuran were added 14.4 g (55.0 mmol) of triphenylphosphine and 4.5 g (55.0 mmol) of 2,2-difluoroethanol at room temperature, followed by stirring. Furthermore, 12.3 g (60.0 mmol) of diisopropyl azodicarboxylate was added thereto under ice-cooling, followed by stirring at room temperature overnight. After the completion of the reaction was confirmed, the reaction solution was poured into water and extracted with ethyl acetate. The resulting organic layer was washed with water and saline, successively, and then dried over anhydrous magnesium sulfate. The solvent was removed by evaporation under reduced pressure and the residue was purified by silica gel column chromatography to obtain 6.8 g (yield: 55.7%) of 1,4-dimethyl-5-(2,2-difluoroethoxy)-3-trifluoromethyl-1H-pyrazole as a pale yellow liquid.

$^1$H-NMR value (CDCl$_3$/TMS δ (ppm)): 6.05(1H, tt, J=3.8, 54.3H z), 4.27(2H, dt, J=3.8, 13.5 Hz), 3.73(3H, s), 2.08(3H, d) Refractive index ($n^D_{20}$): 1.4070

EXAMPLE 22

5-Hydroxy-4-methyl-1-n-propyl-3-trifluoromethyl-1H-pyrazole (Inventive Compound No. 039)

$^1$H-NMR value (CDCl$_3$/TMS δ (ppm)): 8.75(1H, br), 3.94(2H, t), 1.96(3H, d), 1.77(2H, m), 0.88(3H, t) Melting point: 133 to 134° C.

EXAMPLE 23

1-n-Butyl-5-hydroxy-4-methyl-3-trifluoromethyl-1H-pyrazole (Inventive Compound No. 040)

$^1$H-NMR value (CDCl$_3$/TMS δ (ppm)): 7.73(1H, br), 3.98(2H, t), 1.97(3H, d), 1.74(2H, m), 1.29(2H, m), 0.91 (3H, t) Melting point: 132 to 133° C.

EXAMPLE 24

1-tert-Butyl-5-hydroxy-4-methyl-3-trifluoromethyl-1H-pyrazole (Inventive Compound No. 043)

$^1$H-NMR value (CDCl$_3$/TMS δ (ppm)): 5.45(1H, br), 1.97(3H, d), 1.60(9H, s) Melting point: 159 to 160° C.

EXAMPLE 25

5-Difluoromethoxy-4-methyl-1-ethyl-3-trifluoromethyl-1H-pyrazole (Inventive Compound No. 080)

$^1$H-NMR value (CDCl$_3$/TMS δ (ppm)): 6.49(1H, t, J=71.9 Hz), 4.10(2H, q), 2.07(3H, d), 1.42(3H, t) Boiling point: 88 to 91° C./3.73 KPa (28 mmHg) Refractive index ($n^D_{20}$): 1.3971

EXAMPLE 26

1-Ethyl-4-methyl-5-(2,2,2-trifluoroethoxy)-3-trifluoromethyl-1H-pyrazole (Inventive Compound No. 083)

$^1$H-NMR value (CDCl$_3$/TMS δ (ppm)): 4.42 (2H, q), 4.07 (2H, q), 2.09(3H, d), 1.41(3H, t)

EXAMPLE 27

4-Methyl-1-iso-propyl-5-(2,2,2-trifluoroethoxy)-3-trifluoromethyl-1H-pyrazole (Inventive Compound No. 087)

$^1$H-NMR value (CDCl$_3$/TMS δ (ppm)): 4.55(1H, m), 4.41(2H, q), 2.08(3H, d), 1.45(6H, d)

EXAMPLE 28

4-Methyl-1-n-propyl-5-(2,2,2-trifluoroethoxy)-3-trifluoromethyl-1H-pyrazole (Inventive Compound No. 090)

$^1$H-NMR value (CDCl$_3$/TMS δ (ppm)): 4.41(2H, q), 3.97(2H, t), 2.09(3H, d), 1.84(2H, m), 0.91(3H, t)

EXAMPLE 29

1-n-Butyl-4-methyl-5-(2,2,2-trifluoroethoxy)-3-trifluoromethyl-1H-pyrazole (Inventive Compound No. 093)

$^1$H-NMR value (CDCl$_3$/TMS δ (ppm)): 4.41(2H, q), 4.00(2H, t), 2.09(3H, d), 1.80(2H, m), 1.30(2H, m), 0.93 (3H, t)

EXAMPLE 30

1-tert-Butyl-4-methyl-5-(2,2,2-trifluoroethoxy)-3-trifluoromethyl-1H-pyrazole (Inventive Compound No. 102)

$^1$H-NMR value (CDCl$_3$/TMS δ (ppm)): 4.43(2H, q), 2.09(3H, d), 1.59(9H, s)

EXAMPLE 31

4-Ethyl-1-methyl-5-difluoromethoxy-3-trifluoromethyl-1H-pyrazole (Inventive Compound No. 105)

$^1$H-NMR value (CDCl$_3$/TMS δ (ppm) ): 6.50(1H, t, J=71.7 Hz), 3.78(3H, s), 2.51(2H, q), 1.15(3H, t) Refractive index ($n^D_{20}$): 1.4021

EXAMPLE 32

4-Bromomethyl-1-methyl-5-(2,2-difluoroethoxy)-3-trifluoromethyl-1H-pyrazole (Inventive Compound No. 153)

$^1$H-NMR value (CDCl$_3$/TMS δ (ppm) ): 6.11(1H, tt, J=3.5, 54.2 Hz), 4.52(2H, dt, J=3.5, 13.5 Hz), 4.43(2H, s), 3.76(3H, s) Refractive index ($n^D_{20}$): 1.4490

EXAMPLE 33

4-Bromomethyl-1-methyl-5-(2,2,2-trifluoroethoxy)-3-trifluoromethyl-1H-pyrazole (Inventive Compound No. 154)

$^1$H-NMR value (CDCl$_3$/TMS δ (ppm)): 4.68(2H, q), 4.41(2H, s), 3.77(3H, s) Refractive index ($n^D_{20}$): 1.3872

EXAMPLE 34

4-Bromomethyl-5-difluoromethoxy-1-ethyl-3-trifluoromethyl-1H-pyrazole (Inventive Compound No. 155)

$^1$H-NMR value (CDCl$_3$/TMS δ (ppm) ): 6.73 (1H, t, J=71.7 Hz), 4.40(2H, s), 4.13(2H, q), 1.46(3H, t)

EXAMPLE 35

4-Bromomethyl-1-tert-butyl-5-(2,2-difluoroethoxy)-3-trifluoromethyl-1H-pyrazole (Inventive Compound No. 168)

$^1$H-NMR value (CDCl$_3$/TMS δ (ppm)): 6.15(1H, tt, J=3.7, 54.1 Hz), 4.56(2H, dt, J=3.7, 13.4 Hz), 4.45(2H, s), 1.60(9H, s)

EXAMPLE 36

2-(5-(2,2-difluoroethoxy)-1-methyl-3-trifluoromethyl-1H-pyrazole-4-ylmethyl)-isothiourea hydrobromide (Inventive Compound No. 199)

$^1$H-NMR value (CD$_3$OD/TMS δ (ppm)): 6.26(1H, tt, J=3.4, 53.9 Hz), 4.51(2H, dt, J=3.2, 14.1 Hz), 4.41(2H, s), 3.78(3H, s)

EXAMPLE 37

2-(5-(2,2,2-trifluoroethoxy)-1-methyl-3-trifluoromethyl-1H-pyrazole-4-ylmethyl)-isothiourea hydrobromide (Inventive Compound No. 200)

Melting point: 128 to 131° C.

EXAMPLE 38

2-(5-difluoromethoxy-1-ethyl-3-trifluoromethyl-1H-pyrazole-4-ylmethyl)-isothiourea hydrobromide (Inventive Compound No. 201)

Melting point: 139 to 141° C.

EXAMPLE 39

2-(5-difluoromethoxy-1-iso-propyl-3-trifluoromethyl-1H-pyrazole-4-ylmethyl)-isothiourea hydrobromide (Inventive Compound No. 204)

Melting point: 146 to 148° C.

EXAMPLE 40

(5-Difluoromethoxy-1-iso-propyl-3-trifluoromethyl-1H-pyrazole-4-yl)-methanethiol (Inventive Compound No. 223)

$^1$H-NMR value (CDCl$_3$/TMS δ (ppm)): 6.72(1H, t, J=72.2 Hz), 4.60(1H, m), 3.62(2H, s), 1.46(6H, d)

In addition to the above compounds, with respect to the compounds shown by Compound Nos. in the following table, values of physical properties and data of instrumental analysis were confirmed.

TABLE 12

| Compound No. | Value of physical property or NMR data |
|---|---|
| 037 | melting point: 150 to 152° C. |
| 038 | melting point: 150 to 153° C. |
| 151 | $^1$H-NMR value (CDCl$_3$/TMS δ (ppm)): 6.73(1H, t, J=71.5Hz), 4.39(2H, s), 3.82(3H, d) Refractive index (n$^D_{20}$): 1.4401 |
| 178 | melting point: 117 to 119° C. |
| 197 | melting point: 130 to 131° C. |

The following will explain the production of isoxazoline derivatives (described in Japanese Patent Laid-Open No. 308857/2002) using the inventive compounds represented by the general formula [I] as intermediates, and herbicidal action of the isoxazoline derivatives.

First, there will be explained the production of the isoxazoline derivatives (described in Japanese Patent Laid-Open No. 308857/2002) using the inventive compounds represented by the general formula [I].

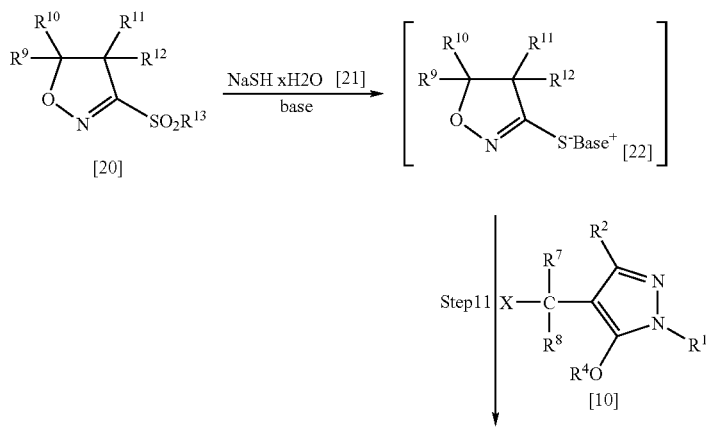

-continued

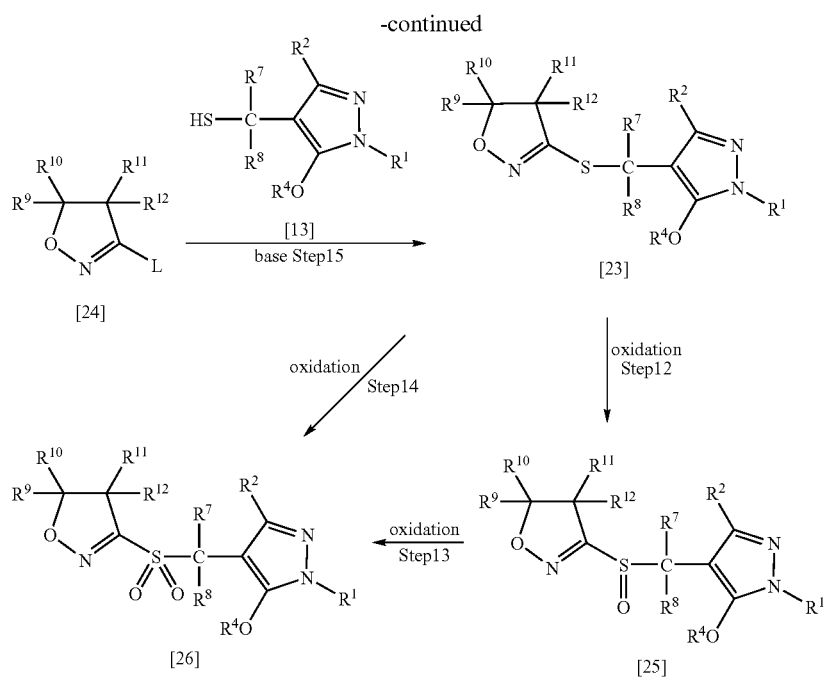

wherein $R^1$, $R^2$, $R^4$, $R^7$, $R^8$, and X represent the same meanings as mentioned above, $R^9$ and $R^{10}$ are the same or different from each other and each represents a hydrogen atom, an alkyl group, a cycloalkyl group, or a cycloalkylalkyl group or $R^9$ and $R^{10}$ are combined together with the carbon atom bonded thereto to form a C3 to C7 spiro ring, $R^{11}$ and $R^{12}$ are the same or different from each other and each represents a hydrogen atom, an alkyl group, or a cycloalkyl group or $R^{11}$ and $R^{12}$ are combined together with the carbon atom bonded thereto to form a C3 to C7 Spiro ring, and further $R^9$, $R^{10}$, $R^{11}$, and $R^{12}$ may form a 5 to 8-membered ring together with the carbon atom bonded thereto. $R^{13}$ represents a C1 to C4 alkyl group, a phenyl group which may be substituted, or a benzyl group which may be substituted and L represents a leaving group such as a halogen atom, a C1 to C4 alkylsulfonyl group, a phenylsulfonyl group which may be substituted, or a benzylsulfonyl group which may be substituted.

The following will explain each step of the above processes for producing isoxazoline derivatives.

(Step 11)

A sulfide derivative represented by the general formula [23] can be produced by reacting a compound represented by the general formula [20] with sodium hydrosulfide hydrate represented by the general formula [21] in a solvent or in the absence of solvent (preferably in a suitable solvent) in the presence of a base to produce a salt of a mercaptan represented by the general formula [22] in the reaction system and then reacting the salt of the mercaptan [22], which was not isolated, with the halogen derivative represented by the general formula [10] which is an inventive compound (optionally, the reaction is conducted under an inert gas atmosphere or a reducing agent can be added).

(Step 12)

A sulfoxide derivative represented by the general formula [25] can be produced by reacting a sulfide derivative represented by the general formula [23] with an oxidizing agent in a suitable solvent.

(Step 13)

A sulfone derivative represented by the general formula [26] can be produced by reacting a sulfoxide derivative represented by the general formula [25] with an oxidizing agent in a suitable solvent.

(Step 14)

The sulfone derivative represented by the general formula [26] can be produced by reacting the sulfide derivative represented by the general formula [23] with a suitable amount of an oxidizing agent in a suitable solvent without isolating the sulfoxide derivative represented by the general formula [25].

(Step 15)

The sulfide derivative represented by the general formula [23] can be produced by reacting a compound represented by the general formula [24] with the mercaptan derivative represented by the general formula [13] which is an inventive compound in a solvent or in the absence of solvent (preferably in a suitable solvent) in the presence of a base (optionally, the reaction is conducted under an inert gas atmosphere or a reducing agent can be added). The mercaptan derivative represented by the general formula [13] which is an inventive compound can be also produced in the reaction system by the method described in Step 6 or 7 of Production Process 5 and then employed.

The following will specifically explain the production of the isoxazoline derivatives (described in Japanese Patent Laid-Open No. 308857/2002) using the inventive compounds represented by the general formula [1] with reference to Reference Examples.

REFERENCE EXAMPLE 1

Production of 3-(5-difluoromethoxy-1-methyl-3-trifluoromethyl-1H-pyrazole-4-ylmethylthio)-5,5-dimethyl-2-isoxazoline 1) To a solution of 6.7 g (35.0 mmol) of 3-ethanesulfonyl-5,5-dimethyl-2-isoxazoline in 50 ml of N,N-dimethylformamide was added 5.6 g (purity: 70%, 70.0 mmol) of sodium hydrosulfide, followed by 1 hour of stirring at room temperature. Thereafter, 4.8 g (35.0 mmol) of potassium carbonate and 10.8 g (35.0 mmol) of 4-bromomethyl-5-difluoromethoxy-1-methyl-3-trifluoromethyl-1H-pyrazole were added thereto, followed by stirring at room temperature overnight. After the completion of the reaction was confirmed, the reaction solution was poured into water and extracted with ethyl acetate. The resulting organic layer was washed with water and saline and then dried over anhydrous magnesium sulfate. The solvent was removed by evaporation under reduced pressure and the residue was purified by silica gel column chromatography to obtain 7.3 g (yield: 57.9%) of 3-(5-difluoromethoxy-1-methyl-3-trifluoromethyl-1H-pyrazole-4-ylmethylthio)-5,5-dimethyl-2-isoxazoline as white crystals (melting point: 39 to 40° C.).

$^1$H-NMR value (CDCl$_3$/TMS δ (ppm)): 6.72(1H, t, J=72.0 Hz), 4.19(2H, s), 3.81(3H, s), 2.78(2H, s), 1.42(6H, s)

2) To a solution of 1.93 g (5.00 mmol) of 2-(5-difluoromethoxy-1-methyl-3-trifluoromethyl-1H-pyrazole-4-ylmethyl)-isothiourea hydrobromide in 10 ml of ethanol were added 0.48 g (12.00 mmol) of sodium hydroxide and 10 ml of -water, followed by 30 minutes of stirring at room temperature. Thereto was added 0.67 g (5.00 mmol) of 3-chloro-5,5-dimethyl-2-isoxazoline at room temperature, followed by further 12 hours of stirring under refluxing. After the completion of the reaction was confirmed, the solvent was removed by evaporation under reduced pressure. The obtained residue was poured into water and extracted with ethyl acetate. The resulting organic layer was washed with water and then dried over anhydrous magnesium sulfate. The solvent was removed by evaporation under reduced pressure and the residue was purified by silica gel column chromatography to obtain 1.02 g (yield: 56.7%) of 3-(5-difluoromethoxy-1-methyl-3-trifluoromethyl-1H-pyrazole-4-ylmethylthio)-5,5-dimethyl-2-isoxazoline.

3) To a solution of 1.93 g (5.00 mmol) of 2-(5-difluoromethoxy-1-methyl-3-trifluoromethyl-1H-pyrazole-4-ylmethyl)-isothiourea hydrobromide in 10 ml of ethanol were added 0.83 g (6.00 mmol) of anhydrous potassium carbonate and 5 ml of water, followed by 30 minutes of stirring at room temperature. Thereto were added a solution of 0.95 g (5.00 mmol) of 3-ethanesulfonyl-5,5-dimethyl-2-isoxazoline in 5 ml of N,N-dimethylformamide and 0.83 g (6.00 mmol) of anhydrous potassium carbonate at room temperature, followed by further 3 hours of stirring at 50° C. After the completion of the reaction was confirmed, the solvent was removed by evaporation under reduced pressure. The obtained residue was poured into water and extracted with ethyl acetate. The resulting organic layer was washed with water and then dried over anhydrous magnesium sulfate. The solvent was removed by evaporation under reduced pressure and the residue was purified by silica gel column chromatography to obtain 1.55 g (yield: 86.1%) of 3-(5-difluoromethoxy-1-methyl-3-trifluoromethyl-1H-pyrazole-4-ylmethylthio)-5,5-dimethyl-2-isoxazoline.

REFERENCE EXAMPLE 2

Production of 3-(5-difluoromethoxy-1-methyl-3-trifluoromethyl-1H-pyrazole-4-ylmethanesulfinyl)-5,5-dimethyl-2-isoxazoline To a solution of 6.2 g (17.3 mmol) of 3-(5-difluoromethoxy-1-methyl-3-trifluoromethyl-1H-pyrazole-4-ylmethylthio)-5,5-dimethyl-2-isoxazoline in 40 ml of chloroform was added 3.4 g (purity: 70%, 13.8 mmol) of m-chloroperbenzoic acid under ice-cooling, followed by 1 hour of stirring. Thereafter, the whole was further stirred at room temperature for 3 hours. After the completion of the reaction was confirmed, the reaction solution was poured into water and extracted with chloroform. The resulting organic layer was washed with an aqueous sodium hydrogen sulfite solution, an aqueous sodium hydrogen carbonate, water, and saline, successively, and then dried over anhydrous magnesium sulfate. The solvent was removed by evaporation under reduced pressure and the resulting solid was washed with n-hexane to obtain 4.1 g (yield: 63.2%) of 3-(5-difluoromethoxy-1-methyl-3-trifluoromethyl-1H-pyrazole-4-ylmethanesulfinyl)-5,5-dimethyl-2-isoxazoline as a white powder (melting point: 112 to 114° C.).

$^1$H-NMR value (CDCl$_3$/TMS δ (ppm)): 6.95(1H, q, J=69.5, 74.4 Hz), 4.16(2H, s), 3.85(3H, s), 3.11(2H, q, J=17.2 Hz), 1.52(6 H, d, J=5.5 Hz)

REFERENCE EXAMPLE 3

Production of 3-(5-difluoromethoxy-1-methyl-3-trifluoromethyl-1H-pyrazole-4-yl-methanesulfonyl)-5,5-dimethyl-2-isoxazoline To a solution of 7.3 g (20.3 mmol) of 3-(5-difluoromethoxy-1-methyl-3-trifluoromethyl-1H-pyrazole-4-ylmethylthio)-5,5-dimethyl-2-isoxazoline in 50 ml of chloroform was added 12.5 g (purity: 70%, 50.8 mmol) of m-chloroperbenzoic acid under ice-cooling, followed by 1 hour of stirring. Thereafter, the whole was further stirred at room temperature overnight. After the completion of the reaction was confirmed, the reaction solution was poured into water and extracted with chloroform. The resulting organic layer was washed with an aqueous sodium hydrogen sulfite solution, an aqueous sodium hydrogen carbonate, water, and saline, successively, and then dried over anhydrous magnesium sulfate. The solvent was removed by evaporation under reduced pressure and the resulting solid was washed with n-hexane to obtain 6.4 g (yield: 80.6%) of 3-(5-difluoromethoxy-1-methyl-3-trifluoromethyl-1H-pyrazole-4-yl-methanesulfonyl)-5,5-dimethyl-2-isoxazoline as a white powder (melting point: 129 to 130° C.).

$^1$H-NMR value (CDCl$_3$/TMS δ (ppm)): 6.83(1H, t, J=71.9 Hz), 4.60(2H, s), 3.88(3H, s), 3.11(2H, s), 1.52(6H, s)

REFERENCE EXAMPLE 4

3-(5-Difluoromethoxy-1-ethyl-3-trifluoromethyl-1H-pyrazole-4-yl-methanesulfonyl)-5,5-dimethyl-2-isoxazoline Melting point: 98 to 100° C.

$^1$H-NMR value (CDCl$_3$/TMS δ (ppm)): 6.83(1H, t, J=72.0 Hz), 4.60(2H, s), 4.19(2H, q), 3.11(2H, s), 1.51(6H, s), 1.49(3H, s)

REFERENCE EXAMPLE 5

3-(5-Difluoromethoxy-1-iso-propyl-3-trifluoromethyl-1H-pyrazole-4-yl-methanesulfonyl)-5,5-dimethyl-2-isoxazoline Refractive index ($n^D_{20}$): 1.4621 $^1$H-NMR value (CDCl$_3$/TMS δ (ppm)): 6.83(1H, t, J=72.1 Hz), 4.70(1H, m), 4.60 (2H, s), 3.10(2H, s), 1.52(6H, s), 1.49(6H, s)

REFERENCE EXAMPLE 6

3-(5-Difluoromethoxy-1-n-propyl-3-trifluoromethyl-1H-pyrazole-4-yl-methanesulfonyl)-5,5-dimethyl-2-isoxazoline Refractive index ($n^D_{20}$): 1.4629 $^1$H-NMR value (CDCl$_3$/TMS δ (ppm)): 6.82(1H, t, J=71.7 Hz), 4.60(2H, s), 4.09 (2H, t), 3.10(2H, s), 1.92(2H, m), 1.52(6H, s), 0.94(3H, t)

REFERENCE EXAMPLE 7

3-(1-iso-Butyl-5-difluoromethoxy-3-trifluoromethyl-1H-pyrazole-4-yl-methanesulfonyl)-5,5-dimethyl-2-isoxazoline Refractive index ($n^D_{20}$): 1.4601 $^1$H-NMR value (CDCl$_3$/TMS δ (ppm)): 6.81(1H, t, J=71.7 Hz), 4.60(2H, s), 3.94 (2H, d), 3.10(2H, s), 2.30(1H, m), 1.51(6H, m), 0.92(6H, d)

REFERENCE EXAMPLE 8

3-(5-Difluoromethoxy-1-methyl-3-trifluoromethyl-1H-pyrazole-4-yl-methanesulfonyl)-5-ethyl-5-methyl-2-isoxazoline Melting point: 77 to 78° C. $^1$H-NMR value (CDCl$_3$/TMS δ (ppm)): 6.83(1H, t, J=71.9 Hz), 4.60(2H, s), 3.88(3H, s), 3.09(2H, ABq, J=17.4 Hz, Δν=46.7 Hz), 1.78(2H, q), 1.47 (3H, s), 0.98(3H, t)

REFERENCE EXAMPLE 9

3-(5-Difluoromethoxy-1-methyl-3-trifluoromethyl-1H-pyrazole-4-yl-methanesulfonyl)-5-methyl-5-cyclopropyl-2-isoxazoline Melting point: 96 to 98° C. $^1$H-NMR value (CDCl$_3$/TMS δ (ppm)): 6.83(1H, t, J=71.9 Hz), 4.59(2H, s), 3.88(3H, s), 3.13(2H, ABq, J=17.3 Hz, Δν=53.4 Hz), 1.48(3H, s), 1.14 (1H, m), 0.36 to 0.58(4H, m)

REFERENCE EXAMPLE 10

7-(5-Difluoromethoxy-1-methyl-3-trifluoromethyl-1H-pyrazole-4-yl-methanesulfonyl)-5-oxa-6-aza-spyro[3.4]-6-octene Melting point: 149 to 151° C. $^1$H-NMR value (CDCl$_3$/TMS δ (ppm)): 6.83(1H, t, J=71.9 Hz), 4.58(2H, s), 3.87 (3H, s), 3.40(2H, s), 2.62(2H, m), 2.27(2H, m), 1.91(1H, m), 1.67(1H, m)

REFERENCE EXAMPLE 11

3-(5-Difluoromethoxy-1-methyl-3-trifluoromethyl-1H-pyrazole-4-yl-methanesulfonyl)-2-isoxazoline Melting point: 115 to 117° C. $^1$H-NMR value (CDCl$_3$/TMS δ (ppm)): 6.83(1H, t, J=71.7 Hz), 4.66(2H, t), 4.61(2H, s), 3.88(3H, s), 3.37(2H, t)

REFERENCE EXAMPLE 12

6-(5-Difluoromethoxy-1-methyl-3-trifluoromethyl-1H-pyrazole-4-yl-methanesulfonyl)-4-oxa-5-aza-spyro[2.4]-5-heptene Melting point: 125 to 126° C. $^1$H-NMR value (CDCl$_3$/TMS δ (ppm)): 6.83(1H, t, J=71.9 Hz), 4.61(2H, s), 3.88 (3H, s), 3.42(2H, s), 1.31(2H, t), 0.91(2H, t)

REFERENCE EXAMPLE 13

3-[1-(5-difluoromethoxy-1-methyl-3-trifluoromethyl-1H-pyrazole-4-yl)-ethanesulfonyl]-5,5-dimethyl-2-isoxazoline Refractive index ($n^D_{20}$): 1.4657 $^1$H-NMR value (CDCl$_3$/TMS δ (ppm)): 6.92(1H, m), 4.83(1H, q), 3.88(3H, s), 3.07(2H, d), 1.83 (3H, d), 1.50(6H, d)

REFERENCE EXAMPLE 14

3-(5-Difluoromethoxy-1-methyl-3-trifluoromethyl-1H-pyrazole-4-yl-methanesulfonyl)-3a,4,5,6,7,7a-hexahydro-benzo [d]isoxazole Melting point: 97 to 98° C. $^1$H-NMR value (CDCl$_3$/TMS δ (ppm)): 6.84(1H, t, J=72.0 Hz), 4.69(1H, m), 4.61(2H, s), 3.88(3H, s), 3.48(1H, m), 1.26 to 2.17(9H, m)

REFERENCE EXAMPLE 15

3-(5-Difluoromethoxy-1-methyl-3-trifluoromethyl-1H-pyrazole-4-yl-methanesulfonyl)-5-methyl-2-isoxazoline Melting point: 106 to 107° C. $^1$H-NMR value (CDCl$_3$/TMS δ (ppm)): 6.83(1H, t, J=71.9 Hz), 5.05(1H, m), 4.60 (2H, s), 3.88(3H, s), 3.44(1H, dd), 2.96(1H, dd), 1.48(3H, d)

REFERENCE EXAMPLE 16

3-(5-Difluoromethoxy-1-methyl-3-trifluoromethyl-1H-pyrazole-4-yl-methanesulfonyl)-5-iso-propyl-2-isoxazoline Melting point: 85 to 86° C. $^1$H-NMR value (CDCl$_3$/TMS δ (ppm)): 6.83(1H, t, J=71.7 Hz), 4.67(1H, m), 4.59(2H, s), 3.88(3H, s), 3.30(1H, dd), 3.08(1H, dd), 1.97(1H, m), 0.98 (6H, dd)

REFERENCE EXAMPLE 17

3-(5-Difluoromethoxy-1-methyl-3-trifluoromethyl-1H-pyrazole-4-yl-methanesulfonyl)-4,5,5-trimethyl-2-isoxazoline Refractive index ($n^D_{20}$): 1.4646 $^1$H-NMR value (CDCl$_3$/TMS δ (ppm)): 6.84(1H, t, J=71.9 Hz), 4.61(2H, q), 3.88 (3H, s), 3.36(1H, q), 1.44(3H, s), 1.38(3H, s), 1.30(3H, d)

REFERENCE EXAMPLE 18

3-(5-Difluoromethoxy-1-methyl-3-trifluoromethyl-1H-pyrazole-4-yl-methanesulfonyl)-4-methyl-2-isoxazoline Refractive index ($n^D_{20}$): 1.4673 $^1$H-NMR value (CDCl$_3$/TMS δ (ppm)): 6.83(1H, t, J=71.8 Hz), 4.71(1H, t), 4.62(2H, q), 4.25(1H, t), 3.88(3H, s), 3.81(1H, m), 1.44(3H, d)

REFERENCE EXAMPLE 19

3-[1-(5-Difluoromethoxy-1-methyl-3-trifluoromethyl-1H-pyrazole-4-yl)-propane-1-sulfonyl]-5,5-dimethyl-2-isoxazoline Refractive index ($n^D_{20}$): 1.4669 $^1$H-NMR value (CDCl$_3$/TMS δ (ppm)): 6.91(1H, t, J=72.9 Hz), 4.60(1H, q), 3.89 (3H, s), 3.05(2H, d), 2.30(2H, m), 1.49(6H, d), 0.94(3H, t)

REFERENCE EXAMPLE 20

3-[5-(2,2,2-Trifluoroethoxy)-1-methyl-3-trifluoromethyl-1H-pyrazole-4-yl-methanesulfonyl]-5,5-dimethyl-2-isoxazoline Melting point: 93 to 95° C. $^1$H-NMR value (CDCl$_3$/TMS δ (ppm)): 4.68(2H, q), 4.59(2H, s), 3.84(3H, s), 3.12(2H, s), 1.53(6H, s)

REFERENCE EXAMPLE 21

3-[5-(2,2-Difluoroethoxy)-1-methyl-3-trifluoromethyl-1H-pyrazole-4-yl-methanesulfonyl]-5,5-dimethyl-2-isoxazoline Melting point: 89 to 91° C. $^1$H-NMR value (CDCl$_3$/TMS δ (ppm)): 6.11(1H, tt, J=3.5, 54.4 Hz), 4.58(2H, s), 4.48(2H, dt, J=3.7, 15.3 Hz), 3.88(3H, s), 3.11(2H, s), 1.52(6H, s)

REFERENCE EXAMPLE 22

3-[1-tert-Butyl-5-(2,2-difluoroethoxy)-3-trifluoromethyl-1H-pyrazole-4-yl-methanesulfonyl]-5,5-dimethyl-2-isoxazoline $^1$H-NMR value (CDCl$_3$/TMS δ (ppm)): 6.14(1H, tt, J=3.9, 54.4 Hz), 4.61(2H, s), 4.54(2H, dt, J=3.6, 13.4 Hz), 3.08(2H, s), 1.63(9H, s), 1.51(6H, s)

REFERENCE EXAMPLE 23

3-[5-(2,2-Difluoroethoxy)-1-iso-propyl-3-trifluoromethyl-1H-pyrazole-4-yl-methanesulfonyl]-5,5-dimethyl-2-isoxazoline Melting point: 88 to 89° C. $^1$H-NMR value (CDCl$_3$/TMS δ (ppm)): 6.11(1H, tt, J=3.4, 54.6 Hz), 4.58 to 4.65(3H, m), 4.47(2H, dt, J=3.7, 13.4 Hz), 3.10 (2H, s), 1.52(6H, s), 1.46(6H, d)

REFERENCE EXAMPLE 24

3-[1-Ethyl-5-(2,2-difluoroethoxy)-3-trifluoromethyl-1H-pyrazole-4-yl-methanesulfonyl]-5,5-dimethyl-2-isoxazoline Refractive index ($n^D_{20}$): 1.4687 $^1$H-NMR value (CDCl$_3$/TMS δ (ppm)): 6.11(1H, tt, J=3.7, 54.5 Hz), 4.58(2H, s), 4.48(2H, dt, J=3.7, 13.4 Hz), 4.16(2H, q), 3.10(2H, s), 1.52(6H, s), 1.47(3H,t)

REFERENCE EXAMPLE 25

3-[5-(2,2-Difluoroethoxy)-1-n-propyl-3-trifluoromethyl-1H-pyrazole-4-yl-methanesulfonyl]-5,5-dimethyl-2-isoxazoline Refractive index ($n_{D20}$): 1.4658 $^1$H-NMR value (CDCl$_3$/TMS δ (ppm)): 6.11(1H, tt, J=3.7, 54.3 Hz), 4.59(2H, s), 4.47(2H, dt, J=3.7, 13.5 Hz), 4.04(2H, t), 3.09(2H, t), 1.90(2H, m), 1.52(6H, s), 0.94(3H, t)

REFERENCE EXAMPLE 26

3-[5-(2,2,2-Trifluoroethoxy)-1-iso-propyl-3-trifluoromethyl-1H-pyrazole-4-yl-methanesulfonyl]-5,5-dimethyl-2-isoxazoline Melting point: 109 to 110° C. $^1$H-NMR value (CDCl$_3$/TMS δ (ppm)): 4.55 to 4.70(5H, m), 3.11 (2H, s), 1.52(6H, s), 1.49(6H, d)

REFERENCE EXAMPLE 27

3-[5-(2,2,2-Trifluoroethoxy)-1-n-propyl-3-trifluoromethyl-1H-pyrazole-4-yl-methanesulfonyl]-5,5-dimethyl-2-isoxazoline Melting point: 49 to 51° C. $^1$H-NMR value (CDCl$_3$/TMS δ (ppm)): 4.68(2H, q), 4.59(2H, s), 4.04(2H, t), 3.11(2H, s), 1.88(2H, m), 1.52(6H, s), 0.94(3 H, t)

REFERENCE EXAMPLE 28

3-[1-n-Butyl-5-(2,2,2-trifluoroethoxy)-3-trifluoromethyl-1H-pyrazole-4-yl-methanesulfonyl]-5,5-dimethyl-2-isoxazoline Refractive index ($n^D_{20}$): 1.4533 $^1$H-NMR value (CDCl$_3$/TMS δ (ppm)): 4.67(2H, q), 4.59(2H, s) 4.07(2H, t), 3.10 (2H, s), 1.84(2H, m), 1.52(6H, s), 1.35(2 H,m), 0.95(3H, t)

REFERENCE EXAMPLE 29

3-[1-Ethyl-5-(2,2,2-trifluoroethoxy)-3-trifluoromethyl-1H-pyrazole-4-yl-methanesulfonyl]-5,5-dimethyl-2-isoxazoline Melting point: 84 to 86° C. $^1$H-NMR value (CDCl$_3$/TMS δ (ppm)): 4.68(2H, q), 4.59(2H, s), 4.14(2H, q), 3.11(2H, s), 1.52(6H, s), 1.47(3H, t)

REFERENCE EXAMPLE 30

3-[1-tert-Butyl-5-(2,2,2-trifluoroethoxy)-3-trifluoromethyl-1H-pyrazole-4-yl-methanesulfonyl]-5,5-dimethyl-2-isoxazoline Melting point: 91 to 92° C. $^1$H-NMR value (CDCl$_3$/TMS δ (ppm)): 4.77(2H, q), 4.60(2H, s), 3.11(2H, s), 1.63(9H, s), 1.52(6H, s)

The following will explain herbicidal action exhibited by the compound represented by the general formula [26] (the isoxazoline derivative described in Japanese Patent Laid-Open No. 308857/2002), which is producible by using the pyrazole derivative represented by the general formula [I] or salt thereof (inventive compound).

In using the compound represented by the general formula [26] (the isoxazoline derivative described in Japanese Patent Laid-Open No. 308857/2002) as a herbicide, the compound may be used by itself but can be also used as formulated in the form of a dust, a wettable powder, an emulsifiable concentrate, a flowable, a microgranule, a granule, or the like by mixing with a carrier, a surfactant, a dispersing agent, an auxiliary agent, or the like which are commonly used for formulation.

Examples of the carrier to be used for the formulation include solid carriers such as talc, bentonite, clay, kaolin, diatomaceous earth, white carbon, vermiculite, calcium carbonate, slaked lime, silica sand, ammonium sulfate, and urea; liquid carriers such as isopropyl alcohol, xylene, cyclohexane, and methylnaphthalene; and the like.

Examples of the surfactant and the dispersing agent include metal salts of alkylbenzenesulfonic acids, metal salts of dinaphthylmethanedisulfonic acid, salts of alcohol sulfate esters, alkylarylsulfonic acid salts, ligninsulfonic acid salts, polyoxyethylene glycol ether, polyoxyethylene alkyl aryl ethers, monoalkylates of polyoxyethylene sorbitan, and the like. Examples of the auxiliary agent include carboxymethyl cellulose, polyethylene glycol, gum arabic, and the like. At the use, it is diluted to an appropriate concentration and then sprayed or applied directly.

The compound represented by the general formula [26] can be used by foliar sparying, soil application, water surface application, or the like. The amount of the active ingredient to be blended is suitably determined according to the necessity. When a powder or a granule is prepared, the amount may be suitably determined in the range of 0.01 to 10% by weight, preferably 0.05 to 5% by weight. When an emulsifiable concentrate or a wettable powder is prepared, the amount may be suitably determined in the range of 1 to 50% by weight, preferably 5 to 30% by weight. When a flowable is prepared, the amount may be suitably determined in the range of 1 to 40% by weight, preferably 5 to 30% by weight.

The amount of the compound represented by the general formula [26] as a herbicide to be applied varies depending upon the kind of the compound used, the target weed, the tendency of weed emergence, the environmental conditions, the form to be used, and the like. When the compound is used per se as in the case of a powder or a granule, the amount is suitably determined in the range of 1 g to 50 kg, preferably 10 g to 10 kg per 1 hectare in terms of the active ingredient. When the compound is used in a liquid form as in the case of an emulsifiable concentrate, a wettable powder, or a flowable, the amount is suitably determined in the range of 0.1 to 50,000 ppm, preferably 10 to 10,000 ppm.

The compound represented by the general formula [26] may be mixed as necessary with an insecticide, a fungicide, other herbicide, a plant growth-regulating agent, a fertilizer, and the like.

The following will explain the formulation method specifically with reference to typical Formulation Examples. The kinds of compounds and additives and their blending ratios are not restricted thereto and can be varied in a wide range. In the following description, "parts" refers to parts by weight.

REFERENCE FORMULATION EXAMPLE 1

Wettable Powder

To 10 parts of the compound represented by the general formula [26] were mixed and pulverized 0.5 part of polyoxyethyleneoctyl phenyl ether, 0.5 part of a sodium salt of β-naphthalenesulfonic acid formalin condensate, 20 parts of diatomaceous earth, and 69 parts of clay, whereby a wettable powder was obtained.

REFERENCE FORMULATION EXAMPLE 2

Flowable

Into 69 parts of water was dispersed 20 parts of a coarsely pulverized compound represented by the general formula [26]. Four parts of a sulfate of a polyoxyethylene styrenated phenyl ether, 7 parts of ethylene glycol were added thereto, and 200 ppm of Silicone AF-118N (manufactured by Asahi Kasei Corporation) was added relative to the formulated product. The resulting mixture was stirred for 30 minutes in a high-speed stirrer and then pulverized in a wet pulverizer to obtain a flowable.

REFERENCE FORMULATION EXAMPLE 3

Emulsifiable Concentrate

To 30 parts of the compound represented by the general formula [26] were added 60 parts of an equal volume mixture of xylene and isophorone and 10 parts of a mixture of surfactants, a polyoxyethylene sorbitan alkylate, a polyoxyethylenealkyl aryl polymer, and an alkyl arylsulfonate. The resulting mixture was thoroughly stirred to obtain an emulsifiable concentrate.

REFERENCE FORMULATION EXAMPLE 4

Granule

Ten parts of water was added to 10 parts of the compound represented by the general formula [26], 80 parts of an extender where talc and bentonite were mixed in a ratio of 1:3, 5 parts of white carbon, and 5 parts of a mixture of surafactants, a polyoxyethylene sorbitan alkylate, a polyoxyethylene alkylaryl polymer, and an alkyl arylsulfonate. The resulting mixture was thoroughly kneaded to form a paste. The paste was extruded through sieve eyes having a diameter of 0.7 mm. The extrudate was dried and then cut into a length of 0.5 to 1 mm to obtain a granule.

The following will explain effects of the compound represented by the general formula [26] with reference to Test Examples.

REFERENCE TEST EXAMPLE 1

Test for Herbicidal Effect by Paddy Field Soil Treatment

A paddy field soil was filled in a plastic pot of 100 cm$^2$ and subjected to puddling. Then, seeds of *Echinochloa oryzicola* Vasing and Monochoria vaginalis var. plantaginea were sowed and water was filled in a depth of 3 cm. Next day, each wettable powder produced in accordance with Formulation Example 1 were diluted with water and dropped on the water surface. The application amount of the wettable powder was 250 g or 1,000 g per 1 hectare in terms of the active ingredient. Then, breeding was made in a greenhouse, and the herbicidal effect of the wettable powder was examined at the 21st day after the treatment in accordance with the standards shown in Table 13. The results are shown in Table 14.

TABLE 13

| Index | Herbicidal effect (extent of growth inhibition) and phytotoxicity |
| --- | --- |
| 5 | A herbicidal effect or phytotoxicity of 90% or more |
| 4 | A herbicidal effect or phytotoxicity of 70% to less than 90 |
| 3 | A herbicidal effect or phytotoxicity of 50% to less than 70% |
| 2 | A herbicidal effect or phytotoxicity of 30% to less than 50% |
| 1 | A herbicidal effect or phytotoxicity of 10% to less than 30% |
| 0 | A herbicidal effect or phytotoxicity of 0% to less than 10% |

TABLE 14

| Reference Example No. | Amount of active ingredient (g a.i./ha) | Echinochloa oryzicola Vasing | Monochoria vaginalis var. plantasinea |
| --- | --- | --- | --- |
| 5 | 1000 | 5 | 5 |
| 8 | 1000 | 5 | 5 |
| 10 | 250 | 5 | 5 |
| 11 | 250 | 5 | 5 |
| 15 | 1000 | 5 | 5 |
| 18 | 250 | 5 | 5 |
| 20 | 1000 | 5 | 5 |
| 21 | 1000 | 5 | 5 |

REFERENCE TEST EXAMPLE 2

Test for Herbicidal Effect by Field Soil Treatment

A field soil was filled in a plastic pot of 80 cm$^2$. Seeds of *Echinochloa crus-galli* var. *crus-galli* and *Setaria viridis* were sowed, followed by covering with the same soil. Each wettable powder produced in accordance with Formulation Example 1 was diluted with water and sprayed uniformly on the soil surface using a small sprayer, in an amount of 1,000 liters per 1 hectare so that the amount of each active ingredient became 250 g or 1,000 g per 1 hectare. Then, breeding was made in a greenhouse, and the herbicidal effect was investigated on the 21st day from the treatment in accordance with the standards shown in Table 13. The results are shown in Table 15.

TABLE 15

| Reference Example No. | Amount of active ingredient (g a.i./ha) | Echinochloa crus-galli var. crus-galli | Setaria viridis |
| --- | --- | --- | --- |
| 3 | 1000 | 5 | 5 |
| 4 | 1000 | 5 | 5 |
| 5 | 1000 | 5 | 5 |
| 8 | 1000 | 5 | 5 |
| 15 | 1000 | 5 | 5 |
| 17 | 1000 | 5 | 5 |
| 20 | 250 | 5 | 5 |
| 24 | 250 | 5 | 5 |

REFERENCE TEST EXAMPLE 3

Test for Herbicidal Effect by Field Foliage Treatment

A sand was filled in a plastic pot of 80 cm$^2$. Seeds of *Echinochloa crus-galli* var. *crus-galli* and *Setaria viridis* were sowed. Breeding was made in a greenhouse for 2 weeks. Each Wettable powder produced in accordance with Formulation Example 1 was diluted with water and sprayed on the whole foliage of plants from above the plants using a small sprayer in an amount of 1,000 liters per 1 hectare so that the amount of the active ingredient became 250 g or 1,000 g per 1 hectare. Then, breeding was made in the greenhouse, and the herbicidal effect was investigated on the 14th day from the treatment in accordance with the standards shown in Table 13. The results are shown in Table 16.

TABLE 16

| Reference Example No. | Amount of active ingredient (g a.i./ha) | Echinochloa crus-galli var. crus-galli | Setaria viridis |
| --- | --- | --- | --- |
| 3 | 1000 | 5 | 5 |
| 6 | 250 | 5 | 4 |
| 7 | 250 | 5 | 4 |
| 9 | 250 | 5 | 4 |
| 13 | 1000 | 5 | 4 |
| 14 | 1000 | 5 | 4 |
| 23 | 250 | 5 | 4 |
| 24 | 250 | 5 | 4 |

INDUSTRIAL APPLICABILITY

According to the present invention, there is provided pyrazole derivatives represented by the general formula [I] or salts thereof, which are useful as production intermediates for isoxazoline derivatives having an excellent herbicidal action (described in Japanese Patent Laid-Open No. 308857/2002). The use of the inventive compounds as production intermediates enables a convenient production of the isoxazoline derivatives having an excellent herbicidal action and described in Japanese Patent Laid-Open No. 308857/2002 with shorter steps (less number of steps) in good total yields. Therefore, the inventive compounds are highly valuable.

The invention claimed is:

1. A pyrazole derivative represented by the general formula [I] or a salt thereof:

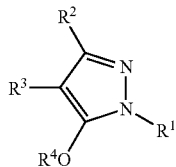

[I]

wherein $R^1$ represents a C1 to C6 alkyl group, $R^2$ represents a C1 to C3 haloalkyl group, $R^3$ represents a hydrogen atom, a C1 to C3 alkyl group which may be substituted with one or more substituents selected from the following substituent group α, or a formyl group, $R^4$ represents a hydrogen atom or a C1 to C3 haloalkyl group, provided that $R^4$ represents a C1 to C3 haloalkyl group in the case that $R^3$ is a hydrogen or a formyl group and $R^4$ is a hydrogen group or a C1 to C3 haloalkyl group in the case that $R^3$ is a C1 to C3 alkyl group which may be substituted with one or more substituents selected from the following substituent group α; "Substituent group α"

halogen atoms, —SH group, —SC(=NH)NH$_2$ group.

2. The pyrazole derivative or salt thereof according to claim 1, wherein $R^4$ is a C1 to C3 haloalkyl group.

3. The pyrazole derivative or salt thereof according to claim 1, wherein $R^3$ is a C1 to C3 alkyl group and $R^4$ is a hydrogen atom.

4. The pyrazole derivative or salt thereof according to claim 1, wherein $R^3$ is a methyl group which may be substituted with one or more substituents selected from the substituent group α.

5. The pyrazole derivative or salt thereof according to claim 1, wherein $R^3$ is a methyl group.

6. A process for producing a pyrazole derivative represented by the general formula [3], comprising a step of reacting a compound represented by the general formula [1] with a compound represented by the general formula [2]:

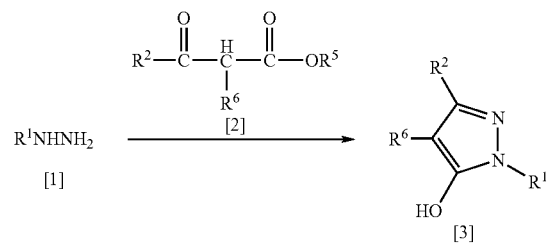

wherein $R^1$ represents a C1 to C6 alkyl group and $R^2$ represents a C1 to C3 haloakyl group, $R^5$ represents a C1 to C3 alkyl group, a phenyl group which may be substituted, or a benzyl group which may be substituted, and $R^6$ represents a C1 to C3 alkyl group.

* * * * *